(12) United States Patent
Ivey et al.

(10) Patent No.: US 12,083,339 B2
(45) Date of Patent: Sep. 10, 2024

(54) INDUCED CELL MORPHOLOGY ELECTROPORATION

(71) Applicants: VIRGINIA TECH INTELLECTUAL PROPERTIES, INC., Blacksburg, VA (US); Wake Forest University Health Sciences, Winston-Salem, NC (US)

(72) Inventors: Jill W. Ivey, Blacksburg, VA (US); Eduardo L. Latouche, Blacksburg, VA (US); Scott S. Verbridge, Blacksburg, VA (US); Rafael V. Davalos, Blacksburg, VA (US); Glenn J. Lesser, Winston-Salem, NC (US); Waldemar Debinski, Blacksburg, VA (US)

(73) Assignees: Virginia Tech Intellectual Properties, Inc., Blacksburg, VA (US); Wake Forest University Health Sciences, Winston-Salem, NC (US)

( * ) Notice: Subject to any disclaimer, the term of this patent is extended or adjusted under 35 U.S.C. 154(b) by 1102 days.

(21) Appl. No.: 16/340,106

(22) PCT Filed: Oct. 6, 2017

(86) PCT No.: PCT/US2017/055634
§ 371 (c)(1),
(2) Date: Apr. 6, 2019

(87) PCT Pub. No.: WO2018/067999
PCT Pub. Date: Apr. 12, 2018

(65) Prior Publication Data
US 2020/0046967 A1 Feb. 13, 2020

Related U.S. Application Data

(60) Provisional application No. 62/405,089, filed on Oct. 6, 2016.

(51) Int. Cl.
*A61N 1/32* (2006.01)
*A61B 18/12* (2006.01)
(Continued)

(52) U.S. Cl.
CPC ............ *A61N 1/327* (2013.01); *A61B 18/12* (2013.01); *A61B 18/1233* (2013.01);
(Continued)

(58) Field of Classification Search
CPC .......... A61P 35/00; A61P 35/02; A61P 35/04; C07K 16/30; A61N 1/327; A61N 1/05;
(Continued)

(56) References Cited

U.S. PATENT DOCUMENTS

2005/0147593 A1* 7/2005 Kinch ............... A61K 38/1709
424/178.1
2010/0023004 A1 1/2010 Francischelli et al.
(Continued)

FOREIGN PATENT DOCUMENTS

| WO | WO-0056395 A1 * | 9/2000 | ........... A61N 1/0412 |
|----|----|----|----|
| WO | 2015/175570 | 11/2015 | |
| WO | 2015175570 A1 | 11/2015 | |

OTHER PUBLICATIONS

Cancer Cytopathology, vol. 123, Issue: 9, pp. 524-530, First published: Sep. 16, 2015, DOI: (10.1002/cncy.21585) (Year: 2015).*
(Continued)

*Primary Examiner* — Linda C Dvorak
*Assistant Examiner* — Lindsay Regan Lancaster
(74) *Attorney, Agent, or Firm* — Carin R. Miller, Esq.; Johnson, Marcou, Isaacs & Nix, LLC

(57) ABSTRACT

Described herein are methods of electroporation that can include the steps of contacting a cell that is responsive to an EphA2 receptor ligand with an amount of an EphA2 receptor ligand and applying high-frequency irreversible elec-
(Continued)

Control.
U-87 MG troporation to the cell. Also described herein are methods of treating cancer in a subject in need thereof, wherein the methods can include the steps of administering an amount of an EphA2 receptor ligand and applying high-frequency irreversible electroporation to a location on or within the subject.

19 Claims, 16 Drawing Sheets

(51) Int. Cl.
    *A61K 38/19*     (2006.01)
    *A61N 1/05*     (2006.01)
    *A61N 1/06*     (2006.01)
    *A61B 17/00*     (2006.01)
    *A61B 18/00*     (2006.01)
    *A61K 38/17*     (2006.01)

(52) U.S. Cl.
    CPC .............. *A61K 38/19* (2013.01); *A61N 1/05* (2013.01); *A61N 1/06* (2013.01); *A61B 2017/00172* (2013.01); *A61B 2018/00613* (2013.01); *A61B 2018/00732* (2013.01); *A61B 2018/00767* (2013.01); *A61B 2018/126* (2013.01); *A61B 2018/128* (2013.01); *A61K 38/1793* (2013.01)

(58) Field of Classification Search
    CPC ...... A61N 1/06; A61B 18/12; A61B 18/1233; A61B 2017/00172; A61B 2018/00613; A61B 2018/00732; A61B 2018/00767; A61B 2018/126; A61B 2018/128; A61K 38/19
    See application file for complete search history.

(56) References Cited

U.S. PATENT DOCUMENTS

| 2012/0109122 | A1* | 5/2012 | Arena | ..................... | A61N 1/327 606/41 |
|---|---|---|---|---|---|
| 2013/0108667 | A1* | 5/2013 | Soikum | .................. | C12N 13/00 977/773 |
| 2015/0289923 | A1 | 10/2015 | Davalos et al. | | |
| 2016/0184003 | A1 | 6/2016 | Srimathveeravalli et al. | | |

OTHER PUBLICATIONS

Weaver, J. C., and Y. A. Chizmadzhev. 1996. Theory of electroporation: a review. Bioelectrochem. Bioenerg. 41:135-160.
Mir, L. M. 2001. Therapeutic perspectives of in vivo cell electropermeabilization. Bioelectrochemistry. 53:1-10.
Agerholm-Larsen, B., H. K. Iversen, ., J. Gehl. 2011. Preclinical validation of electrochemotherapy as an effective treatment for brain tumors. Cancer Res. 71:3753-3762.
Davalos, R. V., I. L. Mir, and B. Rubinsky. 2005. Tissue ablation with irreversible electroporation. Ann. Biomed. Eng. 33:223-231.
Cannon, R., S. Ellis, ., R. C. Martin, II. 2013. Safety and early efficacy of irreversible electroporation for hepatic tumors in proximity to vital structures. J. Surg. Oncol. 107:544-549.
Onik, G., and B. Rubinsky. 2010. Irreversible electroporation: first patient experience focal therapy of prostate cancer. In Irreversible Electroporation. B. Rubinsky, editor. Springer, pp. 235-247.
Martin, R. C., 2nd, D. Kwon, ., K. Watkins. 2015. Treatment of 200 locally advanced (stage III) pancreatic adenocarcinoma patients with irreversible electroporation: safety and efficacy. Ann. Surg. 262:486-494, discussion 492-494.
Neal, R. E., 2nd, J. L. Millar, ., K. R. Thomson. 2014. In vivo characterization and numerical simulation of prostate properties for nonthermal irreversible electroporation ablation. Prostate. 74:458-468.
Lee, E. W., C. Chen, ., S. T. Kee. 2010. Advanced hepatic ablation technique for creating complete cell death: irreversible electroporation. Radiology. 255:426-433.
Guo, Y., Y. Zhang,., A. C. Larson. 2010. Irreversible electroporation therapy in the liver: longitudinal efficacy studies in a rat model of hepatocellular carcinoma. Cancer Res. 70:1555-1563.
Daniels, C., and B. Rubinsky. 2009. Electrical field and temperature model of nonthermal irreversible electroporation in heterogeneous tissues. J. Biomech. Eng. 131:071006.
Lee, E. W., C. T. Loh, and S. T. Kee. 2007. Imaging guided percutaneous irreversible electroporation: ultrasound and immunohistological correlation. Technol. Cancer Res. Treat. 6:287-294.
Bonakdar, M., E. L. Latouche,., R. V. Davalos. 2015. The feasibility of a smart surgical probe for verification of ire treatments using electrical impedance spectroscopy. IEEE Trans. Biomed. Eng. 62:2674-2684.
Neal, R. E., II, J. H. Rossmeisl, Jr., ., R. V. Davalos. 2014. In vitro and numerical support for combinatorial irreversible electroporation and electrochemotherapy glioma treatment. Ann. Biomed. Eng. 42:475-487.
Wykosky, J., D. M. Gibo, ., W. Debinski. 2005. EphA2 as a novel molecular marker and target in glioblastoma multiforme. Mol. Cancer Res. 3:541-551.
Hatano, M., J. Eguchi,., H. Okada. 2005. EphA2 as a glioma-associated antigen: a novel target for glioma vaccines. Neoplasia. 7:717-722.
Liu, D.-P., Y.Wang,., D. Xie. 2007. Ephrin-A1 is a negative regulator in glioma through down-regulation of EphA2 and FAK. Int. J. Oncol. 30:865-871.
Wykosky, J., E. Palma, ., W. Debinski. 2008. Soluble monomeric EphrinA1 is released from tumor cells and is a functional ligand for the EphA2 receptor. Oncogene. 27:7260-7273.
Wykosky, J., D. M. Gibo, and W. Debinski. 2007. A novel, potent, and specific ephrinA1-based cytotoxin against EphA2 receptor expressing tumor cells. Mol. Cancer Ther. 6:3208-3218.
Ferluga, S., R. Hantgan, ., W. Debinski. 2013. Biological and structural characterization of glycosylation on ephrin-A1, a preferred ligand for EphA2 receptor tyrosine kinase. J. Biol. Chem. 288:18448-18457.
Miao, H., E. Burnett, ., B. Wang. 2000. Activation of EphA2 kinase integrin function and causes focal-adhesion-kinase dephosphorylation. Nat. Cell Biol. 2:62-69.
Eppich, H. M., R. Foxall,., D. T. Scadden. 2000. Pulsed electric fields for selection of hematopoietic cells and depletion of tumor cell contaminants. Nat. Biotechnol. 18:882-887.
Agarwal, A., I. Zudans, ., S. G. Weber. 2007. Effect of cell size and shape on single-cell electroporation. Anal. Chem. 79:3589-3596.
Van den Bos, W., D. M. de Bruin, ., J. J. de la Rosette. 2014. The safety and efficacy of irreversible electroporation for the ablation of prostate cancer: a multicentre prospective human in vivo pilot study protocol. BMJ Open. 4:e006382.
Ivey, J.W., E. L. Latouche,., S. S. Verbridge. 2015. Targeted cellular ablation based on the morphology of malignant cells. Sci. Rep. 5: 17157.
Arena, C. B., M. B. Sano, ., R. V. Davalos. 2011. High-frequency irreversible electroporation (H-FIRE) for non-thermal ablation without muscle contraction. Biomed. Eng. Online. 10:102.
Foster, K. R. 2000. Thermal and nonthermal mechanisms of interaction of radio-frequency energy with biological systems. IEEE Trans. Plasma Sci. 28:15-23.
Arena, C. B., M. B. Sano,., R. V. Davalos. 2011. Theoretical considerations of tissue electroporation with high-frequency bipolar pulses. Ieee T Bio-Med Eng. 58:1474-1482.
Cross, V. L., Y. Zheng, ., A. D. Stroock. 2010. Dense type I collagen matrices that support cellular remodeling and microfabrication for studies of tumor angiogenesis and vasculogenesis in vitro. Biomaterials. 31:8596-8607.
Sano, M. B., C. B. Arena, ., R. V. Davalos. 2014. In-vitro bipolar nano- and microsecond electro-pulse bursts for irreversible electroporation therapies. Bioelectrochemistry. 100:69-79.

(56) References Cited

OTHER PUBLICATIONS

Bhonsle, S. P., C. B. Arena, ., R. V. Davalos. 2015. Mitigation of impedance changes due to electroporation therapy using bursts of high-frequency bipolar pulses. Biomed. Eng. Online. 14 (Suppl 3):S3.

White, F. H., and K. Gohari. 1981. Variations in the nuclear-cytoplasmic ration during epithelial differentiation in experimental oralcarcinogenesis. J. Oral Pathol. 10:164-172.

Jin, Y., L. J. Yang, and F. H. White. 1995. Preliminary assessment of the epithelial nuclear-cytoplasmic ratio and nuclear volume density in human palatal lesions. J. Oral Pathol. Med. 24:261-265.

Boyd, A. W., P. F. Bartlett, and M. Lackmann. 2014. Therapeutic targeting of EPH receptors and their ligands. Nat. Rev. Drug Discov. 13:39-62.

Pasquale, E. B. 2010. Eph receptors and ephrins in cancer: bidirectional signalling and beyond. Nat. Rev. Cancer. 10:165-180.

Miao, H., and B. Wang. 2012. EphA receptor signaling—complexity and emerging themes. Semin. Cell Dev. Biol. 23:16-25.

Zelinski, D. P., N. D. Zantek, ., M. S. Kinch. 2001. EphA2 overexpression causes tumorigenesis of mammary epithelial cells. Cancer Res. 61:2301-2306.

Miyazaki, T., H. Kato, ., H. Kuwano. 2003. EphA2 overexpression correlates with poor prognosis in esophageal squamous cell carcinoma. Int. J. Cancer. 103:657-663.

Thaker, P. H., M. Deavers, ., A. K. Sood. 2004. EphA2 expression is associated with aggressive features in ovarian carcinoma. Clin. Cancer Res. 10:5145-5150.

Li, X., Y. Wang, ., X. Zhang. 2007. Expression of EphA2 in human astrocytic tumors: correlation with pathologic grade, proliferation and apoptosis. Tumour Biol. 28:165-172.

Wang, L.-F., E. Fokas, ., H.-X. An. 2008. Increased expression of EphA2 correlates with adverse outcome in primary and recurrent glioblastoma multiforme patients. Oncol. Rep. 19:151-156.

Liu, F., P. J. Park, ., M. D. Johnson. 2006. A genome-wide screen reveals functional gene clusters in the cancer genome and identifies EphA2 as a mitogen in glioblastoma. Cancer Res. 66:10815-10823.

Liu, G., X. Yuan, ., J. S. Yu. 2006. Analysis of gene expression and chemoresistance of CD133þ cancer stem cells in glioblastoma. Mol. Cancer. 5:67.

Binda, E., A. Visioli, ., A. L. Vescovi. 2012. The EphA2 receptor drives self-renewal and tumorigenicity in stem-like tumor-propagating cells from human glioblastomas. Cancer Cell. 22:765-780.

Rubinsky, B. 2007. Irreversible electroporation in medicine. Technology in cancer research & treatment 6:255-259.

Asami, et al., Dielectric Properties of Mouse Lymphocytes and Erythrocytes. Biochim Biophys Acta 1010:49-55.

Yang, J., Y. Huang, X. J. Wang, X. B. Wang, F. F. Becker, and P. R. C. Gascoyne. 1999. Dielectric properties of human leukocyte subpopulations determined by electrorotation as ƒa cell separation criterion. Biophysical Journal 76:3307-3314.

Gascoyne, P. R. C., R. Pethig, J. P. H. Burt, and F. F. Becker. 1993. Membrane-Changes Accompanying the Induced-Differentiation of Friend Murine Erythroleukemia-Cells Studied by Dielectrophoresis. Biochim Biophys Acta 1149:119-126.

Sano, M. B., E. A. Henslee, E. M. Schmelz, and R. V. Davalos. 2011. Contactless dielectrophoretic spectroscopy: Examination of the dielectric properties of cells found in blood. Electrophoresis 32:3164-3171.

Huang, S.-H., L.-Y. Hung, and G.-B. Lee. 2016. Continuous nucleus extraction by optically-induced cell lysis on a batch-type microfluidic platform. Lab on a Chip 16:1447-1456.

\* cited by examiner

Control.

U-87 MG          U-251 MG

DBTRG          NHA eA1 (1μg/mL for ~12 h).

U-87 MG / U-251 MG

DBTRG / NHA

Control.

U-87 MG

U-251 MG

DBTRG

NHA eA1 (1µg/mL for ~12 h).

U-87 MG     U-251 MG

DBTRG       NHA

| Parameter | Symbol | Value | Unit | Reference |
|---|---|---|---|---|
| IRE Voltage | $V_{IRE}$ | 450 | [V] | * |
| H-FIRE Voltage | $V_{HFIRE}$ | 450-700 | [V] | * |
| Electrode Density | $\rho_e$ | 7850 | [kg/m³] | ‡ |
| Electrode Specific Heat Capacity | $Cp_e$ | 475 | [J/(kg·K)] | ‡ |
| Electrode Thermal Conductivity | $k_e$ | 44.5 | [W/(m·K)] | ‡ |
| Electrode Conductivity | $\sigma_e$ | $4.03 \times 10^6$ | [S/m] | ‡ |
| Electrode Permittivity | $\varepsilon_e$ | 1 | | ‡ |
| Hydrogel Density | $\rho_h$ | 997.8 | [kg/m³] | (45) |
| Hydrogel Specific Heat Capacity | $Cp_h$ | 4181.8 | [J/(kg·K)] | (45) |
| Hydrogel Thermal Conductivity | $k_h$ | 0.6 | [W/(m·K)] | (45) |
| Hydrogel Conductivity | $\sigma_h$ | 1.2 | [S/m] | (45) |
| Hydrogel Permittivity | $\varepsilon_h$ | 0 | | (45) |

FIG. 13

| Parameter | Symbol | Value | Units | Reference |
|---|---|---|---|---|
| Media Conductivity | $\sigma_m$ | 0.98 | [S/m] | * |
| Media Permittivity | $\varepsilon_m$ | $80\varepsilon_0$ | [F/m] | ‡ |
| Cytoplasm Conductivity | $\sigma_{cyt}$ | 0.3 | [S/m] | (46) |
| Cytoplasm Permittivity | $\varepsilon_{cyt}$ | $154.4\varepsilon_0$ | [F/m] | (47) |
| Nucleoplasm Conductivity | $\sigma_{nuc}$ | 1.35 | [S/m] | (46) |
| Nucleoplasm Permittivity | $\varepsilon_{nuc}$ | $52\varepsilon_0$ | [F/m] | (46) |
| Cell Membrane Thickness | $t_{mem}$ | $5 \times 10^{-9}$ | [m] | (48) |
| Nuclear Membrane Thickness | $t_{Nmem}$ | $40 \times 10^{-9}$ | [m] | (46) |
| Cell Membrane Conductivity | $\sigma_{mem}$ | $3 \times 10^{-7}$ | [S/m] | (49) |
| Cell Membrane Permittivity | $\varepsilon_{mem}$ | $8.57\varepsilon_0$ | [F/m] | (50) |
| Nuclear Membrane Conductivity | $\sigma_{Nmem}$ | $6 \times 10^{-3}$ | [S/m] | (46) |
| Nuclear Membrane Permittivity | $\varepsilon_{Nmem}$ | $28\varepsilon_0$ | [F/m] | (46) |
| Domain Side Length | $L_d$ | $300 \times 10^{-6}$ | [m] | - |
| Benign Cell Radius | $R_c$ | $20 \times 10^{-6}$ | [m] | * |
| Benign Nuclear Radius | $R_n$ | $6.2 \times 10^{-6}$ | [m] | * |
| Malignant Cell Radius | $R_{mc}$ | $20 \times 10^{-6}$ | [m] | * |
| Malignant Nuclear Radius | $R_{mn}$ | $14.7 \times 10^{-6}$ | [m] | * |
| Malignant Cell Radius (post-ephrin) | $R_{mce}$ | $16.7 \times 10^{-6}$ | [m] | * |
| Malignant Nuclear Radius (post-ephrin) | $R_{mne}$ | $14.7 \times 10^{-6}$ | [m] | * |

FIG. 14

INDUCED CELL MORPHOLOGY ELECTROPORATION

CROSS-REFERENCE TO RELATED APPLICATIONS

This application is the 35 U.S.C. § 371 national stage application of PCT Application No. PCT/US2017/055634, filed Oct. 6, 2017, where the PCT claims priority to, and the benefit of, U.S. provisional application entitled "ENHANCING THE EFFECT OF PULSED ELECTRIC FIELD THERAPY THROUGH INDUCED CELL MORPHOLOGY CHANGES" having Ser. No. 62/405,089, filed Oct. 6, 2016, both of which are herein incorporated by reference in their entireties.

STATEMENT REGARDING FEDERALLY SPONSORED RESEARCH OR DEVELOPMENT

This invention was made with government support under grant number R21CA192042 awarded by the National Cancer Institute, grant number R01CA213423 awarded by the National Institutes of Health, grant number CBET-1652112 awarded by the National Science Foundation, and grant number P30CA012197 awarded by the National Cancer Institute Cancer Center Support Grant. The government has certain rights in the invention.

BACKGROUND

Traditional electroporation modalities for treating and manipulating aberrant cells, such as cancer cells, while generally effective for masses of aberrant cells, are generally unsuitable for use in cases where the aberrant cells are outside of a tumor margin or have otherwise become interspersed with normal health tissue. This is because traditional electroporation modalities cause too much damage to the surrounding normal tissue in these cases for the treatment to be valuable. Often this is the situation with brain cancers and other cancers that are within sensitive tissues, such as the brain. Thus, there exists a need for improved electroporation methods and technologies for selective manipulation and/or treatment of cells.

SUMMARY

Described herein are methods of electroporation that can include the steps of contacting a cell responsive to an EphA2 receptor ligand with an amount of an EphA2 receptor ligand; and applying to the cell responsive to the EphA2 receptor ligand, a high-frequency irreversible electroporation (H-FIRE) pulse train. The H-FIRE pulse train can include one or more bursts of bipolar electric pulses, wherein in each burst can include two or more electric waveform pulses that alternate polarity with each successive electrical waveform pulse, wherein each electric waveform pulse can be separated by a delay between each successive electric waveform pulse, and wherein each electric waveform pulse can have a carrier frequency in the range of about 1 KHz to about 1 MHz. In some aspects, 1 or 2 bursts can be delivered every second. Each electric waveform pulse can be a square wave. The delay between each successive electric waveform pulse can range from about 0.5 µs to about 10 µs. The delay between each successive electric waveform pulse can be about 5 µs. Each electric waveform pulse can be applied for about 250 ns to about 2 µs. Each electric waveform pulse can be applied for about 1 µs. The carrier frequency can be about 200 kHz. An output voltage of the H-FIRE pulse train can range from about 500 V to about 5000 V. The output voltage of the H-FIRE pulse train can results in a voltage-to-distance ratio of about 2000 V/cm. The cell responsive to the EphA2 receptor ligand can be a cell that overexpresses EphA2 receptor as compared to a normal cell. The cell responsive to the EphA2 receptor ligand can be a cancer cell. The cell responsive to the EphA2 receptor ligand can be a malignant cancer cell. The cell responsive to the EphA2 receptor ligand can be a breast cancer cell, melanoma cell, an ovarian cancer cell, a lung cancer cell, a glioma cell, a bladder cancer cell, a prostate cancer cell, an esophageal cancer cell, a renal cancer cell, a colon cancer cell, a pancreatic cancer cell, and/or a vulvar cancer cell. The cell responsive to the EphA2 receptor ligand can be a cell that has about 5% to about a 200% reduction in cytoplasmic size when exposed to the EphA2 receptor ligand and a corresponding increase in the ratio of nucleus to cytoplasmic size (NCR). The EphA2 receptor ligand can be an ephrin. The EphA2 receptor ligand can be ephrin A1. The cell responsive to the EphA2 responsive ligand can be in a subject.

Also described herein are methods of selectively ablating a cell responsive to an EphA2 receptor ligand or population thereof in a subject in need thereof that can include the steps of administering to the subject an amount of an EphA2 receptor ligand; and applying a high-frequency irreversible electroporation (H-FIRE) pulse train to a location on or within the subject. The H-FIRE pulse train can include one or more bursts of bipolar electric pulses, wherein in each burst can include two or more electric waveform pulses that alternate polarity with each successive electrical waveform pulse, wherein each electric waveform pulse can be separated by a delay between each successive electric waveform pulse, and wherein each electric waveform pulse can have a carrier frequency in the range of about 1 kHz to about 1 MHZ. In some aspects, 1 or 2 bursts can be delivered every second. Each of the electric waveform pulse can be a square wave. The delay between each successive electric waveform pulse can range from about 0.5 µs to about 10 µs. The delay between each successive electric waveform pulse can be about 5 µs. Each electric waveform pulse can be applied for about 250 ns to about 2 µs. Each electric waveform pulse can be applied for about 1 µs. The carrier frequency can be about 20 kHz. The output voltage of the H-FIRE pulse train can range from about 500 V to about 5000 V. The output voltage between two or more active electrodes during the H-FIRE pulse train can result in a voltage-to-distance ratio of about 2000 V/cm. The cell responsive to the EphA2 receptor ligand can be a cell that overexpresses EphA2 receptor as compared to a normal cell. The cell responsive to the EphA2 receptor ligand can be a cancer cell. The cell responsive to the EphA2 receptor ligand can be a malignant cancer cell. In some embodiments, the cell responsive to the EphA2 receptor ligand is a breast cancer cell, melanoma cell, an ovarian cancer cell, a lung cancer cell, a glioma cell, a bladder cancer cell, a prostate cancer cell, an esophageal cancer cell, a renal cancer cell, a colon cancer cell, a pancreatic cancer cell, and/or a vulvar cancer cell. The cell responsive to the EphA2 receptor ligand can be a cell that has about 5% to about a 200% reduction in cytoplasmic size when exposed to the EphA2 receptor ligand and a corresponding increase in the ratio of nucleus to cytoplasmic size (NCR). The EphA2 receptor ligand can be an ephrin. The EphA2 receptor ligand can be ephrin A1.

Also described herein are methods of treating cancer in a subject in need thereof that can include the steps of administering to the subject an amount of an EphA2 receptor ligand; and applying a high-frequency irreversible electroporation (H-FIRE) pulse train to a location on or within the subject. The H-FIRE pulse train can include one or more bursts of bipolar electric pulses, wherein in each burst can include two or more electric waveform pulses that alternate polarity with each successive electrical waveform pulse, wherein each electric waveform pulse can be separated by a delay between each successive electric waveform pulse, and wherein each electric waveform pulse can have a carrier frequency in the range of about 1 kHz to about 1 MHz. In some aspects, 1 or 2 bursts can be delivered every second. Each electric waveform pulse is a square wave. The delay between each successive waveform pulse can range from about 0.5 µs to about 10 µs. The delay between each successive waveform pulse is about 5 µs. Each electric wave form pulse can be applied for about 250 ns to about 2 µs. Each electric waveform pulse can be applied for about 1 µs. The carrier frequency can be about 20 kHz. An output voltage of the H-FIRE pulse train can range from about 500 V to about 5000 V. The output voltage between two or more active electrodes during the H-FIRE pulse train can result in a voltage-to-distance ratio of about 2000 V/cm. The cancer can include a cell responsive to the EphA2 receptor ligand. The cancer can include a cell that overexpresses EphA2 receptor as compared to a normal cell. The cancer can be a malignant cancer. The cancer can be a breast cancer cell, melanoma cell, an ovarian cancer cell, a lung cancer cell, a glioma cell, a bladder cancer cell, a prostate cancer cell, an esophageal cancer cell, a renal cancer cell, a colon cancer cell, a prostate cancer cell, a pancreatic cancer cell, or a vulvar cancer cell. The cancer can include a cell that has about 5% to about a 200% reduction in cytoplasmic size when exposed to the EphA2 receptor ligand and a corresponding increase in the ratio of nucleus to cytoplasmic size (NCR). The EphA2 receptor ligand can be an ephrin. The EphA2 receptor ligand can be ephrin A1.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 13 shows a table that can demonstrate the physical properties used in finite element models of hydrogel treatments. * measured values, ‡ default material values in COMSOL.

FIG. 14 shows a table that can demonstrate the physical properties used in a finite element model of single cells. * measured values, ‡ approximation based on water composition.

DETAILED DESCRIPTION

Figure 1A:
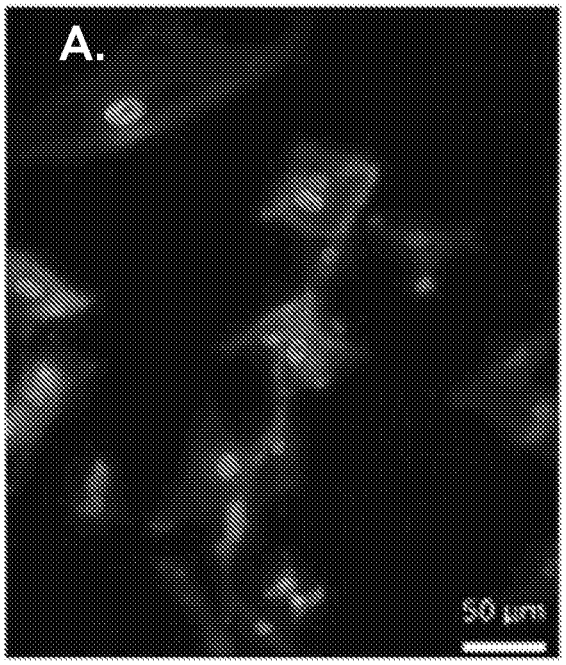
FIGS. 1A-1H show microscopic images of malignant cells stained with DAPI (blue) and phalloidin (red) cultured in control media (FIGS. 1A-1D) or media supplemented with about 1 µg/mL eA1 (FIGS. 1E-1H) for about 12 h. Malignant cells were observed to exhibit cell rounding and a collapse of the cytoplasm around the nucleus, whereas healthy cell morphology remained unchanged upon exposure to eA1. Scale bars=50 µm.
Figure 1B:
Figure 1C:
Figure 1D:
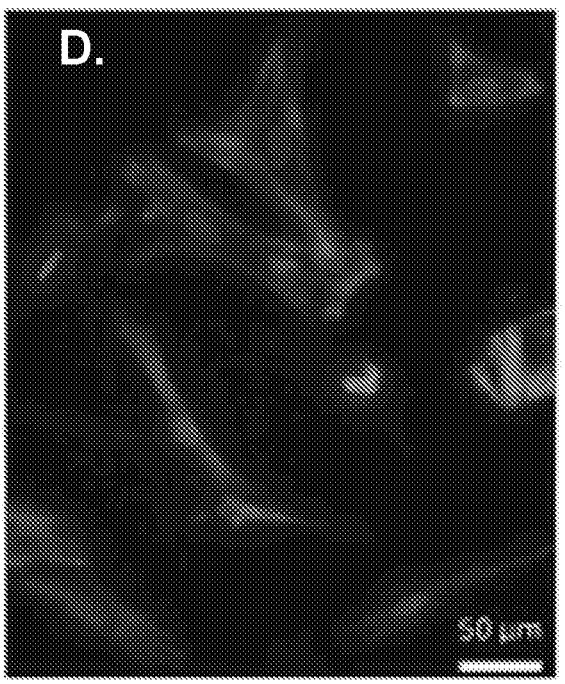
Figure 1E:
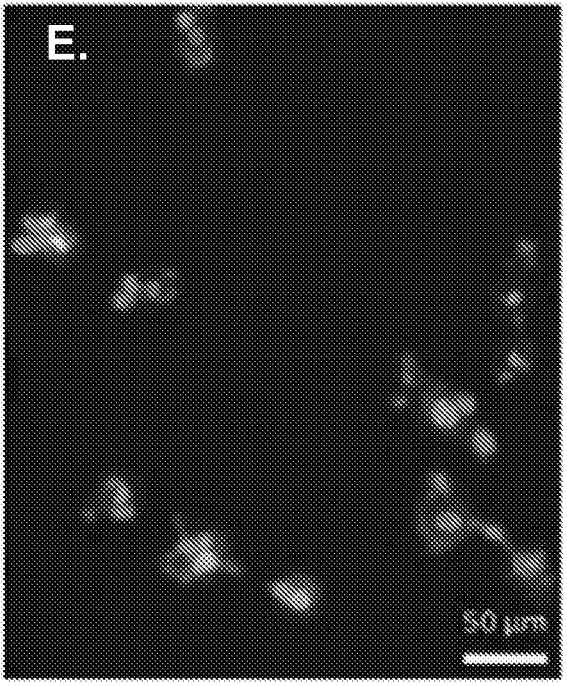
Figure 1F:
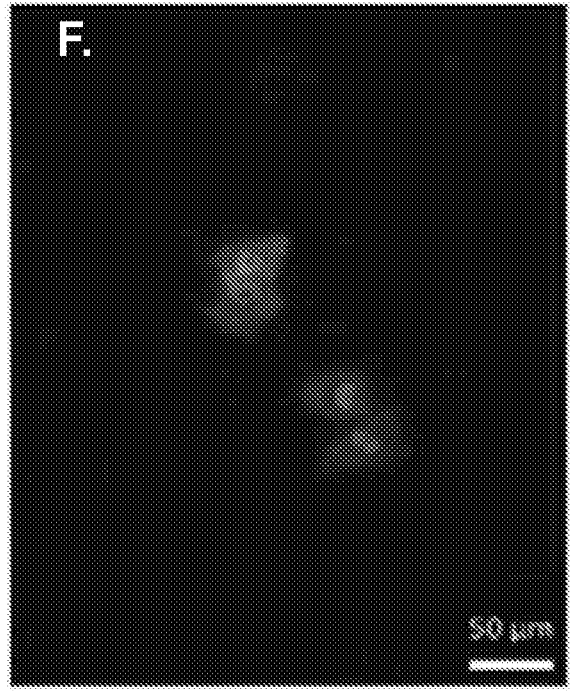
Figure 1G:
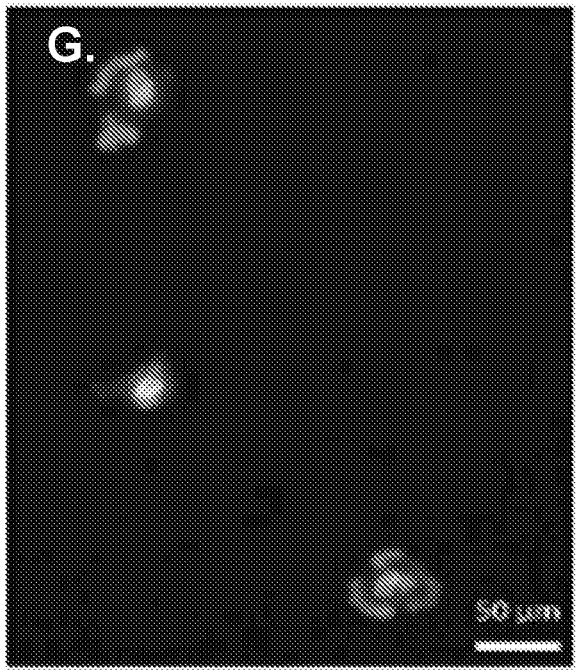
Figure 1H:
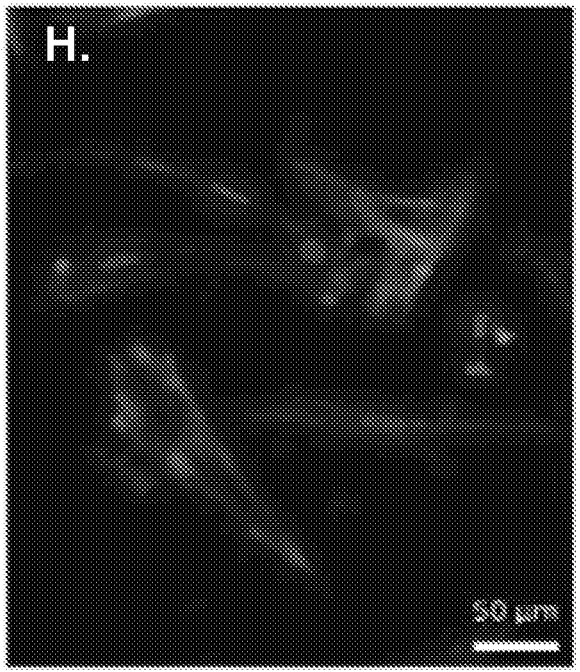

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of cell biology, molecular biology, microbiology, organic chemistry, biochemistry, cancer biology, and the like, which are within the skill of the art. Such techniques are explained fully in the literature.

Definitions

As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "administering" can refer to any administration route, including but not limited to, administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, internasal, intrathecal, intrahepatic, intralesional, and intracranial injections or infusion techniques.

As used herein, "control" can refer to an alternative subject or sample used in an experiment for comparison purposes and included to minimize or distinguish the effect of variables other than an independent variable. A control can be positive or negative.

As used herein, "dose," "unit dose," or "dosage" can refer to physically discrete units suitable for use in a subject, each unit containing a predetermined quantity of a compound as provided herein and/or a pharmaceutical formulation thereof calculated to produce the desired response or responses in association with its administration.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "positive control" can refer to a "control" that is designed to produce the desired result, provided that all reagents are functioning properly and that the experiment is properly conducted.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects, including, but not limited to, killing of a cell, selective killing of a cell responsive to an EphA2 receptor ligand, and/or selective killing of a cancer cell.

As used herein, "therapeutic", "treating", "treat," and the like can refer to include partially or completely delaying, alleviating, mitigating or reducing the intensity of one or more attendant symptoms of a disease or condition including, but not limited to, a cancer, including but not limited to breast cancer, melanomas, ovarian cancer, lung cancers, gliomas, bladder cancers, prostate cancers, esophageal cancer, renal cancer, colon cancer, and vulvar cancers.

As used herein, "responsive to an EphA2 receptor ligand" can refer to cell(s) that demonstrate a decrease in cytoplasmic size and a corresponding increase in the ratio of nucleus size to cytoplasmic size (also expressed herein as nucleus: cytoplasm, NCR). The decrease in cytoplasmic size can be by 1%, 5%, 10%, 20%, 30%, 40%, 50%, 60%, 70%, 80%, 90%, 100%, 125%, 150%, 175%, to 200% or more, and any value or range in between. Responsive cells can be those that have at least a 10%, 20%, 30%, 40%, 50%, 60%, 70%, 80%, 90%, 100%, 125%, 150%, 175%, to 200% or more, including any value or range therein, increase in NCR after exposure to an EphA2 receptor ligand. Responsive cells can be those that overexpress EphA2 as compared to normal, wild-type, and/or otherwise healthy cells for that particular tissue type, organ type, tumor type, structure, developmental stage, disease stage, and/or species. Responsive cells can be identified by exposing the cells to a ligand of EphA2 (e.g. an ephrin) and microscopically observing and measuring using appropriate software (e.g. ImageJ) to determine a reduction in cytoplasmic size and increase in NCR. If the exact cells to be treated are not available, the cells can be determined to be responsive or not by evaluating the response in a related cell type and/or model cell type for which one of ordinary skill in the art would be able to extrapolate the results and reasonably expect the cell type to be treated to also be responsive to an EphA2 ligand. Suitable microscopic and image analysis techniques for measuring changes in cytoplasmic size, nucleus size, and/or cell size are described elsewhere herein and variations of these techniques will be appreciated by those of ordinary skill in the art in view of these techniques described herein. Other suitable techniques to evaluate cytoplasmic size, nucleus size, and/or cell size will be appreciated by those of ordinary skill in the art and are within the scope of this disclosure.

As used herein, "wild-type" is a term of art and can refer the typical phenotype of gene, cell, tissue, and/or species as it occurs on average in a specified population. The term wild-type can refer to a gene, cell, and/or tissue that would be considered normal, non-diseased, or otherwise healthy.

As used herein, "tumor margin" is a term of art and can refer to the margin or edge between malignant tissue and healthy tissue. The tumor margin will be appreciated by one of ordinary skill in the art.

As used herein, "expression" can describe the process undergone by a structural gene to produce a polypeptide. It is a combination of transcription and translation. Expression refers to the "expression" of a nucleic acid to produce a RNA molecule, but it also can refer to "expression" of a polypeptide, indicating that the polypeptide is being produced via expression of the corresponding nucleic acid. Standard techniques for determining expression of a RNA molecule and/or proteins are well known in the art and include without limitation, northern blotting, western blotting, enzyme-linked immunosorbent assays (ELISAs), polymerase chain reaction (PCR)-based techniques (reverse-transcription PCR (RT-PCR), quantitative PCR (qPCR), RT-qPCR, etc.), RNA and protein sequencing, 2D-electrophoresis and mass spectrometry. Further, one of ordinary skill in the art will instant appreciate proper controls to determine expression levels between two or more cells or populations thereof.

As used herein, "overexpression" and "up-regulation" are used interchangeably herein and can refer to the increased expression of a gene or other segment of DNA (as determined by measuring an RNA molecule transcribed from the gene or other segment of DNA) and/or increased expression of a polypeptide as compared to a control, normal, wild-type, non-diseased, and/or otherwise healthy cell or population thereof under substantially similar conditions. Standard techniques for determining expression of a RNA molecule and/or proteins are well known in the art and include without limitation, northern blotting, western blotting, enzyme-linked immunosorbent assays (ELISAs), polymerase chain reaction (PCR)-based techniques (reverse-transcription PCR (RT-PCR), quantitative PCR (qPCR), RT-qPCR, etc.), RNA and protein sequencing, 2D-electrophoresis and mass spectrometry. Further, one of ordinary skill in the art will instant appreciate proper controls to determine expression levels between two or more cells or populations thereof. Overexpression can be found where there is about 2, 3, 4, 5, 6, 7, 8, 9, 10, 20, 30, 40, 50, 60, 70, 80, 90, 100 or more fold greater expression of an RNA molecule and/or polypeptide in a cell as compared to a control, normal, wild-type, non-diseased, and/or otherwise healthy cell or population thereof.

As used herein, "underexpression" and "down-regulation" are used interchangeably herein and can refer to the decreased expression of a gene or other segment of DNA (as determined by measuring an RNA molecule transcribed from the gene or other segment of DNA) and/or decreased expression of a polypeptide as compared to a control, normal, wild-type, non-diseased, and/or otherwise healthy cell or population thereof under substantially similar conditions. Standard techniques for determining expression of a RNA molecule and/or proteins are well known in the art and include without limitation, northern blotting, western blotting, enzyme-linked immunosorbent assays (ELISAs), polymerase chain reaction (PCR)-based techniques (reverse-transcription PCR (RT-PCR), quantitative PCR (qPCR), RT-qPCR, etc.), RNA and protein sequencing, 2D-electrophoresis and mass spectrometry. Further, one of ordinary skill in the art will instant appreciate proper controls to determine expression levels between two or more cells or populations thereof. Underexpression can be found where there is about 2, 3, 4, 5, 6, 7, 8, 9, 10, 20, 30, 40-, 50, 60, 70, 80-, 90, 100 or more fold less expression of an RNA molecule and/or polypeptide in a cell as compared to a control, normal, wild-type, non-diseased, and/or otherwise healthy cell or population thereof.

As used herein, "gene" can refer to a hereditary unit corresponding to a sequence of DNA that occupies a specific location on a chromosome and that contains the genetic instruction for a characteristic(s) or trait(s) in an organism.

As used herein, "selective ablation" can refer to ablating cells with a certain characteristic or set thereof while not ablating others that do not have the requisite characteristic(s) even though all cells received substantially the same conditions resulting in ablation of cells with the requisite characteristic(s). In some aspects herein, the requisite conditions for ablation can be being responsive to an EphA2 receptor ligand, overexpressing an EphA2 receptor, being a cancer cell, and/or being a malignant cancer cell.

Unless otherwise defined herein, all technical and scientific terms used herein have the same meaning as commonly understood by one of ordinary skill in the art. Standard techniques for determining expression of a RNA molecule and/or proteins are well known in the art and include without limitation, northern blotting, western blotting, enzyme-linked immunosorbent assays (ELISAs), polymerase chain reaction (PCR)-based techniques (reverse-transcription PCR (RT-PCR), quantitative PCR (qPCR), RT-qPCR, etc.), RNA and protein sequencing, 2D-electrophoresis and mass spectrometry. Further, one of ordinary skill in the art will instant appreciate proper controls to determine expression levels between two or more cells or populations thereof.

Discussion

Electroporation can describe the phenomenon of using an electric field to permeabilize the membrane of a cell by inducing a transmembrane potential large enough to induce a disruption in the lipid bilayer. Electroporation can be reversible or irreversible. In reversible electroporation, an electric filed is applied to the cell(s) to induce a change in the transmembrane potential (TMP) such that the TMP reaches a threshold value of about 250 mV. At this point transient nanoscale pores form in the cell membrane, allowing the passage of otherwise excluded molecules through the membrane barrier. The change in TMP is not so great that the cell cannot recover from the electroporation. Reversible electroporation has been traditionally used for gene transfection, gene therapy, and cancer electrochemotherapy (ECT).

In irreversible electroporation (IRE) an electric filed is used to permeabilize the membrane of a cell such that the cell cannot recover from the permeabilization and dies. In IRE, the change in TMP induced by the applied electric field is such that the cell cannot recover from the pore formation due to loss of homeostasis. In IRE, the threshold TMP value is typically about 1 V. IRE has traditionally been used as a cell or tissue ablation technique for the treatment of a variety of disorders, including a variety of cancers, including prostate, pancreas, and liver cancers (5-8).

Although IRE as a cancer treatment method has many advantages over other approaches, such as cell-scale resolution and sparing the extracellular matrix and other vital structures (e.g. blood vessels) while producing a more uniform ablation, IRE still suffers from several disadvantages. IRE methods do not allow for the treatment of diffuse cells outside the tumor margin without ablation of healthy tissue, a situation especially problematic where such invasive cells are interspersed and/or adjacent to sensitive tissues, cells, and/or other structures, such as in the brain.

To increase the selective capabilities of IRE treatment, here we investigate a new combinatorial treatment concept, combining electroporation with a molecular therapy that it was hypothesized would act in a synergistic manner to the physical treatment. Previous research efforts have identified the receptor EphA2 as a promising target for selective molecular treatment for GBM (15). EphA2, a member of the largest class of receptor tyrosine kinases, is overexpressed in GBM tissue in a predominantly inactive state (15), as its preferred ligand ephrinA1 (eA1) is present at diminished levels compared to the level in normal brain tissue (16, 17). Research efforts have shown that exogenous soluble eA1 is a functional ligand for EphA2 (18), and progress has been made in creating ephrin-based therapeutic agents through conjugation of a bacterial toxic protein to soluble eA1 that selectively targets GBM cells (19). From this work developing an ephrin-based molecular targeted therapy, a selective morphology change in GBM cells upon exposure to eA1 was observed. This physical response is characterized by a rounding of the cell and a shrinking of the cell cytoplasm (18, 20, 21).

In considering IRE, the physical attributes of a cell are important, as electroporation is dependent on both cell size and morphology. The effect of cell size on electroporation has been demonstrated for a variety of pulse widths ranging from a few microseconds (22) to hundreds of milliseconds (23). The steady-state scenario is valid for the understanding of electroporation phenomenon involved in typical IRE protocols used in the treatment of cancer. These protocols involve the application of around 90 pulses of 50-100 μs duration delivered through electrodes inserted into the tissue (5, 24). It has been shown that by reducing the duration of the electric field pulses to be shorter than the charging time of the cell membrane, the field can penetrate the cell interior, and the dependence of electroporation on cell size is reduced (25, 26).

This shorter pulse technique, termed high-frequency IRE (H-FIRE), which uses trains of about ≤2 μs duration bipolar pulses, exposes inner organelles to large electric fields. H-FIRE acts on cells in such a way that nuclear size becomes a more important predictor of cell death than cell size, with a lower electric field needed to kill cells with a higher nuclear/cytoplasm ratio (NCR) (25).

With these deficiencies in mind, described herein are methods to selectively ablate cells that are responsive to an EphA2 receptor ligand. In some aspects, the responsive cells can be those that overexpress the EphA2 receptor. In some aspects, the method can include the steps of administering a EphA2 receptor ligand to a cell or population thereof, where and applying a pulsed high frequency electric field to the cell, such that the cell(s) present in the population that are responsive to an EphA2 receptor ligand are selectively ablated. One advantage of the methods described herein as compared to traditional IRE and H-FIRE methods can be enhanced selectivity of ablation of cells that are responsive to an EphA2 receptor ligand, which can be diseased cells (e.g. cancer cells), over normal or otherwise healthy cells. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Methods of Enhancing Selectivity of Electroporation

Cell size can impact performance of electroporation. For example, larger cells are generally easier to permeabilize using traditional reversible electroporation techniques and easier to kill using traditional IRE. Likewise, smaller cells are more difficult to permeabilize using traditional reversible electroporation techniques and more difficult to kill using traditional IRE. The ratio of the nucleus to the cytoplasm size (NCR) in larger cells is smaller as compared to smaller cells, for cells with similarly sized nuclei, because smaller cells typically have less cytoplasmic volume. It is similarly observed that cells with a smaller NCR (e.g. cells with a larger total size) are more susceptible to traditional reversible electroporation and traditional IRE techniques than cells with a larger NCR (e.g. cells with a smaller total size).

EphA2 receptor is a member of the Eph tyrosine kinase receptor family. EphA2 is normally expressed in many tissue types but has been demonstrated to be overexpressed in many cancer types as compared to otherwise normal (healthy) cells. See e.g. Tandon et al. 2011. Expert Opin. Ther. Targets. 15(1). For example, EphA2 has been shown to be overexpressed in breast cancer, melanomas, ovarian cancer, lung cancers, gliomas, bladder cancers, prostate cancers, esophageal cancer, renal cancer, colon cancer, pancreatic, and vulvar cancers. See e.g. Tandon et al. 2011.

In some cases, cells that are responsive to an EphA2 receptor ligand, including but not limited to cells that overexpress EphA2 receptor, can be interspersed within a population of normal (or otherwise healthy) cells making them difficult to ablate using traditional IRE techniques. In some cases these are cells that can lie outside the tumor margin, can be malignant cells that have infiltrated remote tissues, or can be tumors that are otherwise not candidates for traditional ablation techniques due to proximity, for example, to sensitive areas or tissue types where ablation of these sensitive areas would result in deleterious effects.

With these general principles in mind, described herein are electroporation methods that can enhance selective ablation and/or ECT by high-frequency IRE (H-FIRE) in cells that can be responsive to EphA2 receptor ligand. Generally, cells that can be responsive to an EphA2 receptor ligand can be contacted with a EphA2 receptor ligand. Activation of the EphA2 receptor by its ligand can induce physical changes in the cell, including shrinkage of the cytoplasm. Shrinkage of the cytoplasm can result in an increase in the NCR of the cell. As discussed above, an increase in the NCR of the cell makes the cell less susceptible to traditional IRE and reversible electroporation techniques. However, the increase in the NCR of the cells increases the susceptibility of the cell to H-FIRE. As compared to H-FIRE alone, the methods described herein can produce an increased sensitivity to H-FIRE allowing for improved selectivity between diseased cells responsive to EphA2 and normal cells (otherwise healthy cells). By increasing the sensitivity of cells overexpressing EphA2, the H-FIRE conditions can be such that they are less deleterious to normal cells, thus allowing for ablation of cells overexpressing EphA2 (e.g. cancerous cells) that have infiltrated healthy tissue and/or reside outside of a tumor margin.

In some aspect the electroporation methods can include contacting a cell responsive to an EphA2 receptor ligand with an amount of an EphA2 receptor ligand and applying to the cell responsive to the EphA2 receptor ligand, a high-frequency irreversible electroporation (H-FIRE) pulse train. In some aspects, the H-FIRE pulse train can include one or more bursts of bipolar electric pulses, wherein in each burst can include two or more electrical waveform pulses that alternate polarity with each successive electrical waveform pulse.

The number of bursts can range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, to 100 or more, including any value or range therein. Each electric waveform pulse can be separated by a delay between each successive electric waveform pulse. Each electric waveform pulse can have a carrier frequency in the range of about 1 kHz to about 1 MHz or any value or range therein. In some aspects, the carrier frequency is about 1-10 kHz, 10-100 kHz, 100-250 kHz, 250-500 kHz, 500-1000 kHz, 1000 kHz to about 1 MHz. In some aspects, the carrier frequency is about 20 KHz.

One, 2, 3, 4, 5, 6, 7, 8, 9, 10 or more bursts can be delivered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59 seconds. One or more bursts can be delivered every 1, 2, 3, 4, 5, 6, 7, 8, 9 10, or more minutes. The total number of bursts that can be delivered can range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, to 100 or more and any range therein. In some aspects about 1-100, 1-75, 1-50, 1-25, 1-10, or about 50 bursts are delivered in total at a rate of 1-5, 1-2, or 1 burst per second.

Each of electric waveform pulse can be any suitable waveform. In some aspects, each electric waveform pulse can be a square wave. The delay between each successive electric waveform pulse can range from about 0.5 µs to about 10 µs or any specific value or range therein. In some aspects, the delay between each successive electric waveform pulse can be about 0.5 µs to about 1 µs, about 1 µs to about 2 µs, about 2 µs to about 4 µs, about 5 µs to about 7 µs, about 8 µs to about 10 µs, or about 5 µs. Each electrical wave form pulse can be applied for ≤ about 2 µs. In some aspects, each electrical waveform pulse can be applied for about 250 ns to about 2 µs or any value or range therein. In some aspects, each electrical waveform pulse can be applied for about 1 µs.

An output voltage of the H-FIRE pulse train can range from 500 V to about 5000 V. In some aspects, the output voltage of the H-FIRE pulse train can be about 700 V. In some aspects, the output voltage of the H-FIRE pulse train can result in a voltage-to-distance ratio of about 2000 V/cm.

Other suitable H-FIRE protocols and parameters can be as in U.S. Patent Application Publication No. 2012/0109122 A1 and International Patent Application Publication No. WO 2015/175570 A1. The H-FIRE pulse train can be delivered by any suitably configured electroporation system, including but not limited to those set forth in U.S. Patent Application Publication No. 2012/0109122 A1 and International Patent Application Publication No. WO 2015/175570 A1.

The cell responsive to the EphA2 receptor ligand can be a cell that overexpresses EphA2 receptor as compared to a normal cell. The cell responsive to the EphA2 receptor ligand can be a cancer cell. The cell responsive to the EphA2 receptor ligand can be a malignant cancer cell. The cell responsive to the EphA2 receptor ligand can be a breast cancer cell, melanoma cell, an ovarian cancer cell, a lung cancer cell, a glioma cell, a bladder cancer cell, a prostate cancer cell, an esophageal cancer cell, a renal cancer cell, a colon cancer cell, a pancreatic cancer cell, and/or a vulvar cancer cell. The cell responsive to the EphA2 receptor ligand can be a cell that has about 5% to about a 200% reduction in cytoplasmic size when exposed to the EphA2 receptor ligand and a corresponding increase in the ratio of nucleus to cytoplasmic size (NCR). The cell responsive to the EphA2 receptor ligand can be a cell that has at least a 10% increase in the NCR when exposed to the EphA2 receptor ligand.

In some aspects, the EphA2 receptor ligand is an ephrin. In some aspects the EphA2 receptor ligand is ephrinA1 (eA1). The EphA2 receptor ligand can be included in a pharmaceutical formulation that can include an amount of the EphA2 receptor ligand or pharmaceutically acceptable salt thereof and a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations that include the EphA2 receptor ligand can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

The amount of the EphA2 receptor ligand or pharmaceutically acceptable salt thereof contained in a pharmaceutical formulation can range from about 0.001 micrograms to about 1000 grams and any value or range therein. In some aspects, the amount of the EphA2 receptor ligand or pharmaceutically acceptable salt thereof can range from about 0.001 micrograms to about 0.01 micrograms and any value or range therein. In other aspects, the amount of the EphA2 receptor ligand or pharmaceutically acceptable salt thereof can range from about 0.01 micrograms to about 0.1 micrograms and any value or range therein. In further aspects, the amount of the EphA2 receptor ligand or pharmaceutically acceptable salt thereof can range from about 0.1 micrograms to about 1.0 grams and any value or range therein. In yet further aspects, the amount of the EphA2 receptor ligand or pharmaceutically acceptable salt thereof can range from about 1.0 grams to about 10 grams and any value or range therein. In other aspects, the amount of the EphA2 receptor ligand or pharmaceutically acceptable salt thereof can range from about 10 grams to about 100 grams and any value or range therein. In still other aspects, the amount of the EphA2 receptor ligand or pharmaceutically acceptable salt thereof can range from about 100 grams to about 1000 grams and any value or range therein.

The amount of the EphA2 receptor ligand or pharmaceutically acceptable salt thereof can range from about 0.01 IU to about 1000 IU and any value or range therein. The amount of the EphA2 receptor ligand or pharmaceutically acceptable salt thereof can range from 0.001 mL to about 1000 mL and any value or range therein. The amount of the EphA2 receptor ligand or pharmaceutically acceptable salt thereof can range from about 1% w/w to about 99.9% w/w and any value or range therein of the total pharmaceutical formulation. The amount of the EphA2 receptor ligand or pharmaceutically acceptable salt thereof can range from about 1% v/v to about 99.9% v/v and any value or range therein of the total pharmaceutical formulation. The amount of the EphA2 receptor ligand or pharmaceutically acceptable salt thereof can range from about 1% w/v to about 99.9% w/v and any value or range therein of the total pharmaceutical formulation.

In some embodiments, the pharmaceutical formulations described herein can be in a dosage form. The dosage form can be administered to a subject in need thereof. In some embodiments, the subject in need thereof can have one or more cells responsive to a EphA2 receptor ligand.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intraventricular, intraarticular, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. The subject in need thereof can have one or more cells responsive to an EphA2 receptor ligand.

Where appropriate, the dosage forms described herein can be microencapsulated. The dosage form can also be prepared to prolong or sustain the release of any ingredient. In some embodiments, the compound or derivative thereof is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Weiterstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, compound, derivative thereof, auxiliary active ingredient, and/or pharmaceutically acceptable salt thereof are incorporated into a liposome. In some embodiments, a compound, derivative thereof, auxiliary active ingredient, and/or pharmaceutically acceptable salts thereof is integrated into the lipid membrane of the liposome. In other embodiments, a compound, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation. The liposomal formulation can be administered to a subject in need thereof. The subject in need thereof can have one or more cells responsive to an EphA2 receptor ligand.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the compound, derivative thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators. The nasal/inhalation formulations can be administered to a subject in need thereof. The subject in need thereof can have one or more cells responsive to an EphA2 receptor ligand.

In some embodiments, the dosage forms are aerosol formulations suitable for administration by inhalation. In some of these embodiments, the aerosol formulation contains a solution or fine suspension of a compound, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof. The subject in need thereof can have one or more cells responsive to an EphA2 receptor ligand.

For some dosage forms suitable and/or adapted for inhaled administration, the pharmaceutical formulation is a dry powder inhalable formulations. In addition to the compound, derivative thereof, auxiliary active ingredient, and/or pharmaceutically acceptable salt thereof, such a dosage form can contain a powder base such as lactose, glucose, trehalose, mannitol I, and/or starch. In some of these embodiments, the compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some aspects, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof. The subject in need thereof can have one or more cells responsive to an EphA2 receptor ligand.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof. The subject in need thereof can have one or more cells responsive to an EphA2 receptor ligand.

For some embodiments, the dosage form contains a predetermined amount of a compound and/or derivative thereof per unit dose. In other embodiments, the predetermined amount of the compound and/or derivative thereof can be an appropriate fraction of the total amount or the EphA2 receptor ligand to be administered prior to H-FIRE treatment. Such unit doses may therefore be administered once or more than once a day (e.g. 1, 2, 3, 4, 5, 6, or more times per day). Such pharmaceutical formulations may be prepared by any of the methods well known in the art.

In some aspects the cell responsive to EphA2 receptor ligand is in a subject. The cell responsive to EphA2 receptor ligand cane within a tumor. The cell responsive to EphA2 receptor ligand can be within a tumor margin. The cell responsive to EphA2 receptor ligand can be interspersed within normal and/or cells not responsive to an EphA2 receptor ligand. The cell responsive to EphA2 receptor ligand can be in any tissue or organ type.

Accordingly, the methods described herein can selectively ablate a cell responsive to an EphA2 receptor ligand or population thereof in a subject in need thereof. The methods can be applied to a cell and/or subject in need thereof as many times as needed and/or desired. In some aspects the methods can be applied to a cell and/or a subject in need thereof 1, 2, 3, 4, 5, 6, 7, 8, 9, 10, 11, 12, 13, 14, 15, 16, 17, 18, 19, 20 time or more per day, week, month, and/or year.

Insofar as many cancer cell types are cells that can overexpress EphA2 receptor, and thus can be responsive to a EphA2 receptor ligand, also described herein are methods of treating cancer in a subject in need thereof that can include the step of administering to the subject an amount of an EphA2 receptor ligand or pharmaceutical formulation thereof; and applying a high-frequency irreversible electroporation (H-FIRE) pulse train to a location on or within the subject. The H-FIRE can be applied to the same location where the EphA2 receptor ligand was administered, such that the cells being treated with the H-FIRE have also been exposed to the EphA2 receptor ligand. This allows for localized selective ablation even if administration of the EphA2 receptor ligand is systemic. The cancer to be treated can include one or more cells that are responsive to the EphA2 receptor ligand. The cancer to be treated can include a cell that overexpresses EphA2 receptor as compared to a normal cell. The cancer to be treated can be a malignant cancer. The cancer can be a breast cancer cell, melanoma cell, an ovarian cancer cell, a lung cancer cell, a glioma cell, a bladder cancer cell, a prostate cancer cell, an esophageal cancer cell, a renal cancer cell, a colon cancer cell, a pancreatic cell, and/or a vulvar cancer cell. The cancer can include a cell that has about 5% to about a 200% reduction in cytoplasmic size when exposed to the EphA2 receptor ligand and a corresponding increase in the ratio of nucleus to cytoplasmic size (NCR). The cancer can include a cell that has at least a 10% increase in NCR when exposed to the EphA2 receptor ligand. Suitable EphA2 receptor ligand(s) and pharmaceutical formulation thereof are described elsewhere herein.

Administration can be local or systemic. Administration of the EphA2 receptor ligand or pharmaceutical formulation thereof can be systemic or localized to a desired area. Administration of the EphA2 receptor ligand can be by any suitable method or route. Appropriate administration routes include, but are not limited to, oral (including buccal or sublingual), rectal, intraocular, inhaled, intranasal, topical (including buccal, sublingual, or transdermal), vaginal, parenteral, subcutaneous, intraventricular, intraarticular, intramuscular, intravenous, internasal, and intradermal.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Electroporation can describe the phenomenon of using an electric field to permeabilize the membrane of a cell by inducing a transmembrane potential large enough to induce a disruption in the lipid bilayer. Once the transmembrane potential reaches a threshold value of about 250 mV, transient nanoscale pores form in the membrane, allowing the passage of otherwise excluded molecules through the membrane barrier (1). This reversible electroporation technique has been used for gene transfection, gene therapy, and cancer electrochemotherapy (ECT) (2, 3). When the transmembrane potential reaches another threshold value of about 1 V, the cell cannot recover from the pore formation and dies due to loss of homeostasis (4). This method of cell ablation, termed irreversible electroporation (IRE), has been used for the treatment of a variety of cancers, including prostate, pancreas, and liver cancers (5-8).

IRE as a cancer treatment method has many advantages over other approaches. The non-thermal nature of the treatment allows for the sparing of extracellular matrix and vital structures such as blood vessels while producing a more uniform ablation due to the lack of a heat-sink effect (9). IRE ablation methods are able to achieve cell-scale (about 50 mm) resolution between ablated and non-ablated zones (9, 10), allowing for ablation regions to be predicted by pre-treatment planning (11). In addition, real-time monitoring by imaging and impedance measurements can be done to ensure proper electrode placement and complete ablation (12, 13). Although the benefits of this treatment modality have underpinned its successful use for a variety of cancers, invasive cancers such as glioblastoma (GBM) still present challenges. IRE methods do not allow for the treatment of diffuse cells outside the tumor margin without ablation of healthy tissue, a situation especially problematic in the brain. To address these challenges and improve selectivity outside the tumor margin, investigators have begun studying combination therapies such as IRE used with ECT (14).

To increase the selective capabilities of IRE treatment, here we investigate a new combinatorial treatment concept, combining electroporation with a molecular therapy that it was hypothesized would act in a synergistic manner to the physical treatment. Previous research efforts have identified the receptor EphA2 as a promising target for selective molecular treatment for GBM (15). EphA2, a member of the largest class of receptor tyrosine kinases, is overexpressed in GBM tissue in a predominantly inactive state (15), as its preferred ligand ephrinA1 (eA1) is present at diminished levels compared to the level in normal brain tissue (16, 17). Research efforts have shown that exogenous soluble eA1 is a functional ligand for EphA2 (18), and progress has been made in creating ephrin-based therapeutic agents through conjugation of a bacterial toxic protein to soluble eA1 that selectively targets GBM cells (19). From this work developing an ephrin-based molecular targeted therapy, a selective morphology change in GBM cells upon exposure to eA1 was observed. This physical response is characterized by a rounding of the cell and a shrinking of the cell cytoplasm (18, 20, 21).

In considering IRE, the physical attributes of a cell are important, as electroporation is dependent on both cell size and morphology. The effect of cell size on electroporation has been demonstrated for a variety of pulse widths ranging from a few microseconds (22) to hundreds of milliseconds (23). The steady-state scenario is valid for the understanding of electroporation phenomenon involved in typical IRE protocols used in the treatment of cancer. These protocols involve the application of around 90 pulses of 50-100 μs duration delivered through electrodes inserted into the tissue (5, 24). It has been shown that by reducing the duration of the electric field pulses to be shorter than the charging time of the cell membrane, the field can penetrate the cell interior, and the dependence of electroporation on cell size is reduced (25, 26).

This shorter pulse technique, termed high-frequency IRE (H-FIRE), which uses trains of about ≤2 μs duration bipolar pulses, exposes inner organelles to large electric fields. H-FIRE acts on cells in such a way that nuclear size becomes a more important predictor of cell death than cell size, with a lower electric field needed to kill cells with a higher nuclear/cytoplasm ratio (NCR) (25).

Despite some efforts to predict the transmembrane potential (TMP) of cells exposed to pulsed electric fields (PEFs) on the order of a few microseconds, no mathematical models for cells of a high NCR have been developed (27, 28). This Example investigates the effects of cell size and morphology on the electroporation phenomenon at short pulse lengths, where the steady-state electroporation equation breaks down and frequency is known to play an important role in predicting induced TMP. This Example also examines the NCR effect on H-FIRE ablation by combining H-FIRE therapy with a molecular intervention using eA1 to increase NCR.

The overabundance of EphA2 receptor and the diminished presence of eA1 in GBM tissue open up this receptor-ligand interaction as a unique method for selectively tuning cell morphology to isolate the NCR effect on H-FIRE. This Example can therefore be a model for selectively ablating GBM and other cells that can also be responsive to a EphA2 ligand, such as eA1, with respect to NCR. This Example can also demonstrate that electroporation efficacy can be increased by decreasing cell size, which can also highlight the complexities ignored by the Schwan equation in describing cell response to electric fields with short pulses.

Materials and Methods

Cell culture. U-87 MG human GBM cells (ATCC, Manassas, VA) were cultured in Dulbecco's modified Eagle's medium (DMEM) containing about 10% fetal bovine serum (FBS) and about 1% penicillin/streptomycin (PS). Normal human astrocyte (NHA) cells (Lonza, Basel, Switzerland) were cultured in astrocyte growth media (Lonza). U-251 MG primary human GBM cells (ATCC) cells were grown in DMEM containing about 10% FBS, about 1% PS, and about 0.1 mM non-essential amino acid. DBTRG human glioblastoma cells (ATCC) were cultured in RPMI medium containing about 10% FBS, about 2 mM L-glutamine, about 1% PS, and about 0.1 mM non-essential amino acids. All cells were grown in culture at about 37° C. in about 5% $CO_2$ in a humidified incubator. Cells were seeded in hydrogels at a density of about $1 \times 10^6$ cells/mL. The hydrogels were submerged in appropriate growth media for the cell type at about 37° C. in about 5% $CO_2$ in a humidified incubator, and cell viability was maintained within hydrogels for up to about 7 days.

Construction of Collagen Scaffolds. Stocks of type I collagen were prepared by dissolving rat tail tendon in acetic acid, followed by freezing and lyophilization, as described previously (29). Stock solution concentrations of collagen were created at a density of about 10 mg/mL. Scaffolds with a final concentration of about 5 mg/mL were made from concentrated collagen stocks to create collagen gels of about 0.5% (w/w). Neutralized collagen solutions were created by mixing acid-dissolved collagen with 10×DMEM (10% of total collagen solution volume) and sufficient volumes of about 1 N NaOH until a pH in the range of about 7.0-7.4 was achieved. The neutralized collagen was mixed with cells suspended in DMEM or NHA media to achieve a cell density of $1 \times 10^6$ cells/mL in the final collagen mixture. Solutions were mixed carefully with a sterilized spatula to ensure homogenous distribution throughout the gel without damaging cells. Collagen solutions were then dispensed into a polydimethylsiloxane (PDMS) mold with a cut-out of 10 mm diameter and 1 mm depth and molded flat to ensure consistent scaffold geometry. Previous mathematical modeling and experiments on oxygen ($O_2$) consumption rates by tumor cells (29) confirms that at this cell density and scaffold thickness, $O_2$ concentration is uniform throughout the scaffold depth. Collagen was allowed to polymerize at about 37° C. and about 5% $CO_2$ for 30 min.

Figure 12B:
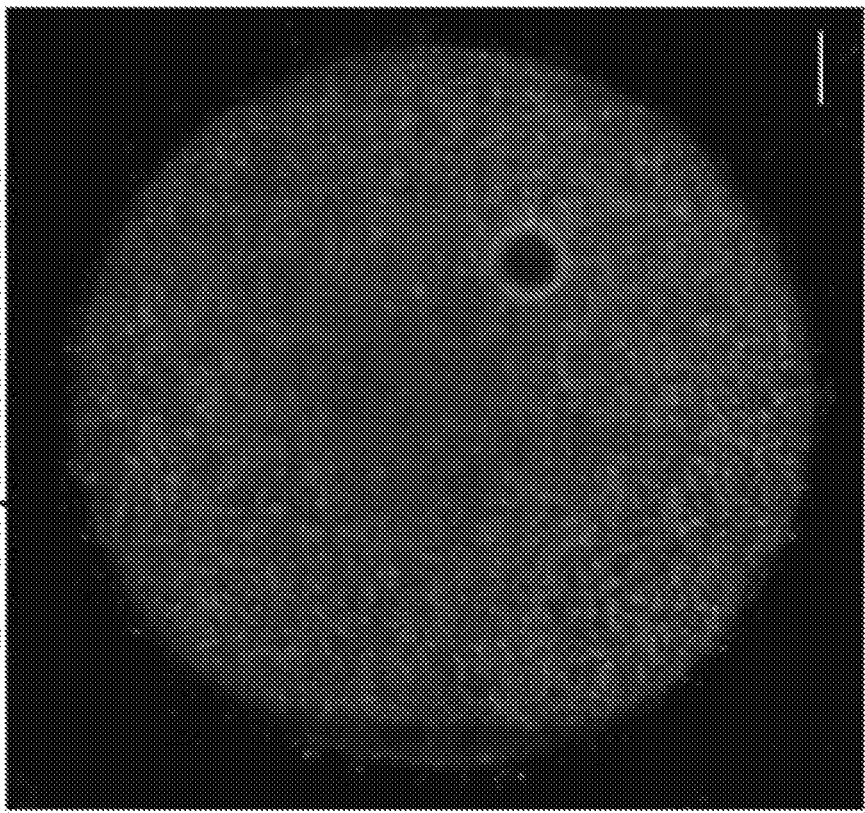
FIGS. 12A-12B shows microscopic images demonstrating results from live-dead staining of cells cultured with eA1 in hydrogels. Cells were cultured in collagen hydrogels in control media (FIG. 12A) or media supplemented with about 1 µg/mL eA1 for about 12 h, which was then replaced with basal media and cells were cultured out to 14 days (FIG. 12B). Calcein AM staining of the live cells (green) and ethD-III staining of dead cells (red) shows no visible cell death for eA1 treatment. Scale bar=1 mm.
Figure 12A:
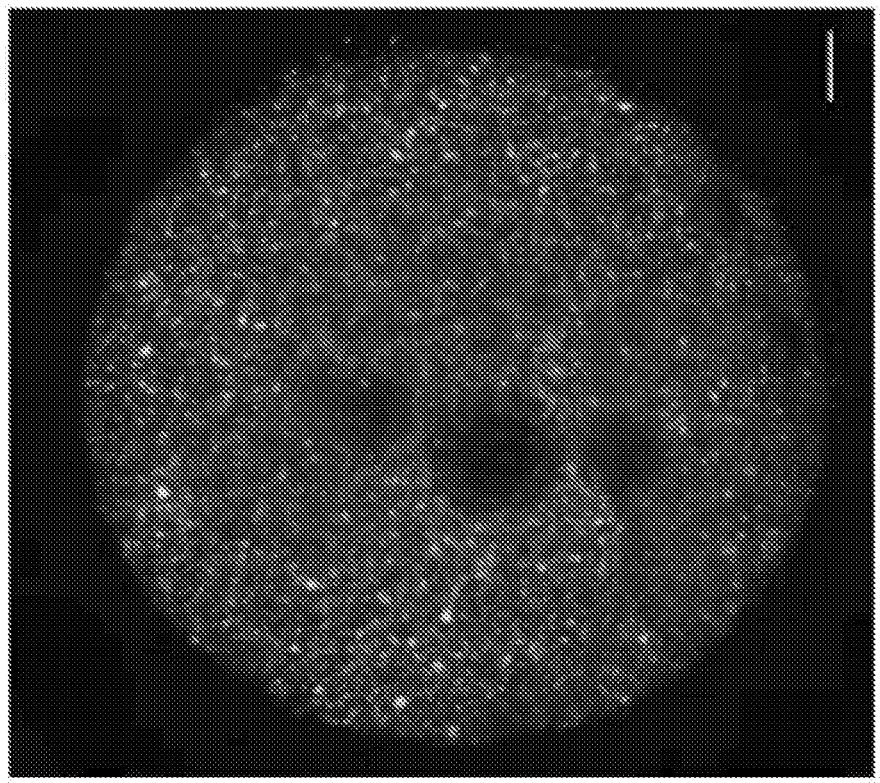

Treatment with eA1. Cells seeded in collagen hydrogels were cultured for about 24 h after seeding to allow for cells to engage the collagen and achieve a physiologically relevant morphology. After about 24 h, hydrogels in the eA1-treated condition were cultured in serum-free cell culture media with about 1 mg/mL eA1-FC (R&D Systems) added to the media for about 12 h before electroporation treatment or fixation for immunofluorescence staining. Control cells were cultured in hydrogels submerged in serum-free culture media without the added eA1-FC for about 12 h before use in experiments. The about 12 h time point was chosen because a full morphological change of the cells within the hydrogels was seen by about 12 h and no further changes were observed at longer exposure times. No difference was seen in viability between hydrogels cultured in eA1-FC conditioned media and control media before exposure to electroporation therapy (FIGS. 12A-12B).

Fluorescent Staining. U-87, U251, DBTRG, and NHA cells were individually seeded in hydrogels described previously. After culturing the cells for about 24 h for engagement with the matrix and then for an additional about 12 h after treatment, the hydrogels were fixed using 4% formalin and blocked and permeabilized using about 40 mg/mL bovine serum albumin (BSA) and about 0.05% Triton-X. Cellular F-actin was stained with Alexa Fluor 568 phalloidin (Life Technologies, Carlsbad, CA), whereas cell nuclei were stained with diaminophenylindole (DAPI; Sigma-Aldrich, St. Louis, MO). Cells were visualized using a Zeiss LSM880 (Carl Zeiss Microscopy, Thornwood, NY) laser scanning confocal microscope.

Determination of the NCR. Untreated hydrogels seeded at the same cell density and collagen conditions as treated hydrogels were fixed and fluorescently stained to determine overall cell area and nuclear area for cells in the control condition and in the ephA1-treated condition. Measurements were made on at least four cells per hydrogel, and at least five hydrogels were analyzed for each condition so at least 20 cells were used to determine average NCR for each cell type in each condition. Image analysis was done in Image J (National Institutes of Health, Bethesda, MD). Z-stack images were converted to 2D projection images and cell measurements were made from these projections. NCR was calculated from the measured cell area ($A_C$) and nuclear area ($A_N$) as in Equation 1.

$$NCR = \frac{A_N}{A_C - A_N} \qquad \text{Equation (1)}$$

Finite-element analysis in hydrogels. Finite-element models using COMSOL Multiphysics (Version 4.3; COMSOL, Palo Alto, CA) were used to solve the Laplace equation to find the electric field distribution within the hydrogels for each different voltage used. The electric field distribution within the hydrogel was found by solving the Laplace equation (Equation 2), $$\nabla^2 \phi = 0 \qquad \text{(Equation 2)}$$

where $\phi$ is the electrical potential. The boundaries of one electrode were set to the applied voltage ($\phi = V_{applied}$) and the boundaries of the second electrode were set to ground ($\phi = 0$) while the initial voltage ($V_0$) for all subdomains was set to 0 V. All other external boundaries were set to electrical insulation ($-n \cdot J = 0$). The mesh was refined until error between successive refinements was <1%. The final mesh contained 47,438 elements, and solutions were found in about 3 min on a Pentium i3 processor.

Finite-element Analysis of Individual Cells Based on NCR. The electrodynamic solutions of interest were reached by modeling a spherical cell membrane and nuclear envelope and solving a finite-element model with an impedance boundary condition scheme as previously described (25,30). The models used to investigate the membrane response to different pulse parameters changed the NCR based on representative cell geometries determined based on average measurements made in ImageJ image analysis software (National Institutes of Health) from confocal microscopy images. To better understand the effect of high-frequency components of H-FIRE on individual cells, a frequency-dependent module was used to mimic the increase in frequency for different H-FIRE pulse lengths and IRE-type pulses. The geometry and physical properties of the cell can be found in FIG. 13.

Simulations were solved in the frequency domain using an electric-currents module, which has been previously shown to correlate well for spherical cells exposed to rectangular pulses in the order of 1-2 µs (28). To account for the impedance posed by the membranes of the cell and nucleus, their boundaries were assigned impedance properties found in the literature (FIG. 14).

Electroporation Techniques. Pulsed electroporation experiments were performed in collagen hydrogels with constant electrical properties. High-frequency pulses were delivered using a custom-built pulse generation system (INSPIRE 2.0; VoltMed, Blacksburg, VA). Pulses were delivered through custom-built electrodes composed of two solid stainless steel cylinders with diameters of 0.87 mm separated by 3.3 mm edge to edge, with spacing and geometry maintained by a three-dimensional printed electrode holder. In the H-FIRE pulsing protocol, treatments were performed delivering 50 bursts of 1 µs bipolar pulses. A burst consisted of 100×1 µs pulses of alternating polarity with a 5 µs inter-pulse delay delivered with a repetition rate of one burst per second. Voltage output was set to 700 V to achieve measurable lesions within the hydrogel geometry. Conventional IRE pulses were delivered using an ECM 830 pulse generator (Harvard Apparatus, Holliston, MA) through the same custom-built electrodes. These treatments consisted of 50 square pulses of 100 µs pulse width with a repetition rate of one pulse per second. IRE voltage output was set to 350 V to achieve measurable lesions within the hydrogel geometry.

Determination of Lethal Threshold in Hydrogels. The thresholds for cell death were determined by first performing a live-dead stain on the hydrogels about 24 h after delivering treatment. Live cells were stained with calcein AM (Biotium, Hayward, CA) and fluoresced as green, whereas dead cells were stained with ethidium homodimer III (Biotium) and fluoresced as red. The size of the red-stained dead region was measured using ImageJ image analysis software. Geometric measurements of the ablation zones were mapped to a finite-element model to calculate the electric field during treatments of the scaffolds. The electric field magnitude at the edge of the live and dead regions was considered the electric field threshold for cell death for the given cell type. Each individual hydrogel exposed to either H-FIRE therapy or H-FIRE-with-eA1 therapy measured to determine the lethal electric field for the cell type was considered an independent sample representing the response of about 125,000 cells. For each condition, hydrogels were pulsed in at least three different independent experiments on different days.

Power Spectral Analysis. A power spectral analysis was conducted by running a fast Fourier transform on the experimental H-FIRE pulses. The power spectral analysis was used to determine the dominant frequencies a cell is exposed to upon treatment, as demonstrated elsewhere as a tool for understanding bipolar pulses (31).

Statistical Analysis. Statistical significance was determined by a two-tailed t-test performed in Prism Statistical Software (Version 6; Graphpad, La Jolla, CA). A 95% confidence interval was used, with significance defined as $p < 0.05$. All numerical results are reported as the mean 5 SD of all experimental measurements. No outliers were excluded.

Results.

Figure 2:
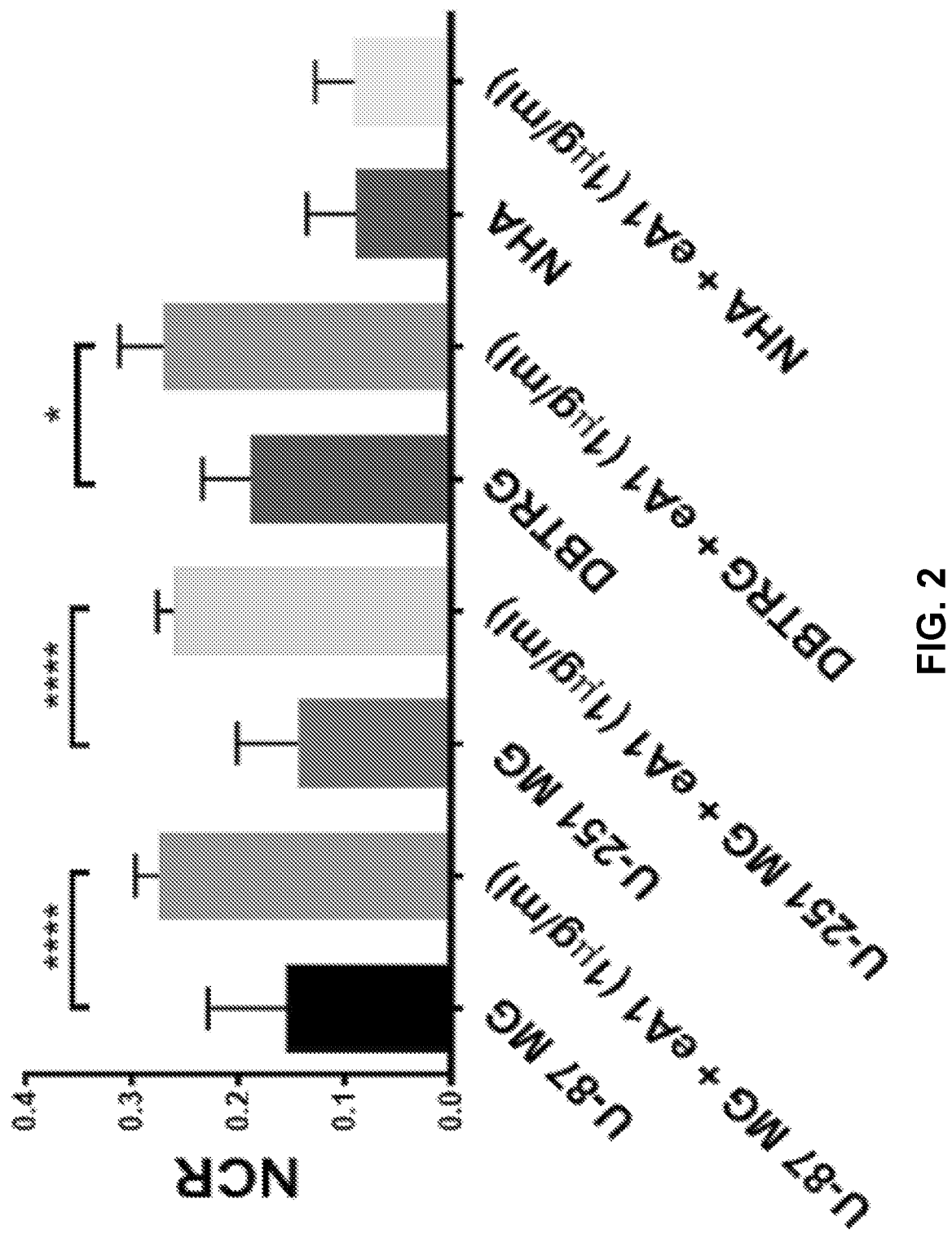
FIG. 2 shows a graph that can demonstrate the effect of eA1-induced cell morphology change on NCR (nucleus to cytoplasm) in malignant and normal cells. n=20; ****p≤ 0.0001, *p=0.027. A quantitative increase in NCR in malignant cells was observed. NCR was observed to be unchanged in normal astrocytes.

EphA2 activation by eA1 can induce a targeted morphology change in malignant cells. To investigate the dynamics of eA1-induced morphology changes, malignant GBM and normal brain cells were cultured in three-dimensional hydrogels and exposed them to eA1. EphA2 activation by eA1 in malignant cell lines (U-87 MG, U-251 MG, and DBTRG) were observed to lead to visible cell morphology changes characterized by cell rounding and a collapse of the cytoplasm (FIGS. 1A-1H). Cell rounding was visible after 6 h of culture in media containing eA1 (about 1 mg/mL), with the full morphological change accomplished by about 12 h. In NHA cells, no morphological change was observed at any time point out to 48 h when culturing hydrogels in eA1 media. For the malignant cell lines, the cytoplasm collapse upon EphA2 activation resulted in a significant change in the NCR of the cells (FIG. 2). NHA cells showed no significant change in NCR under these treatment conditions. No morphology change was observed in control tumor cells cultured in media without eA1 present.

Extent of electroporation for different cell morphologies is dependent on frequency of the electric field. Finite-element modeling was used to predict the induced TMP for a variety of cell morphologies as a function of the frequency of a steady-state, alternating-current electric field. Characteristic morphologies determined from experimental culture of glioma cells, normal astrocytes, and glioma cells treated with eA1 were used. At lower frequencies, characteristic of IRE pulse waveforms, larger cells experience a greater induced transmembrane potential compared with a glioma cell that shrinks in volume due to treatment with eA1. At a frequency of about 10 kHz, the enlarged nucleus of the glioma cell causes it to experience a greater transmembrane potential than an astrocyte of the same size but with a smaller nucleus. This trend continued throughout higher frequencies of electric field, suggesting that fields of frequency >10 kHz can be used to accomplish greater electroporation in cells with a larger nucleus than in cells with a smaller nucleus. At an electric field frequency of about 100 kHz, the smaller cell experiences a larger induced transmembrane potential than the larger cells, suggesting a greater extent of electroporation in smaller cells with an enlarged nucleus than in larger cells.

Figure 3:
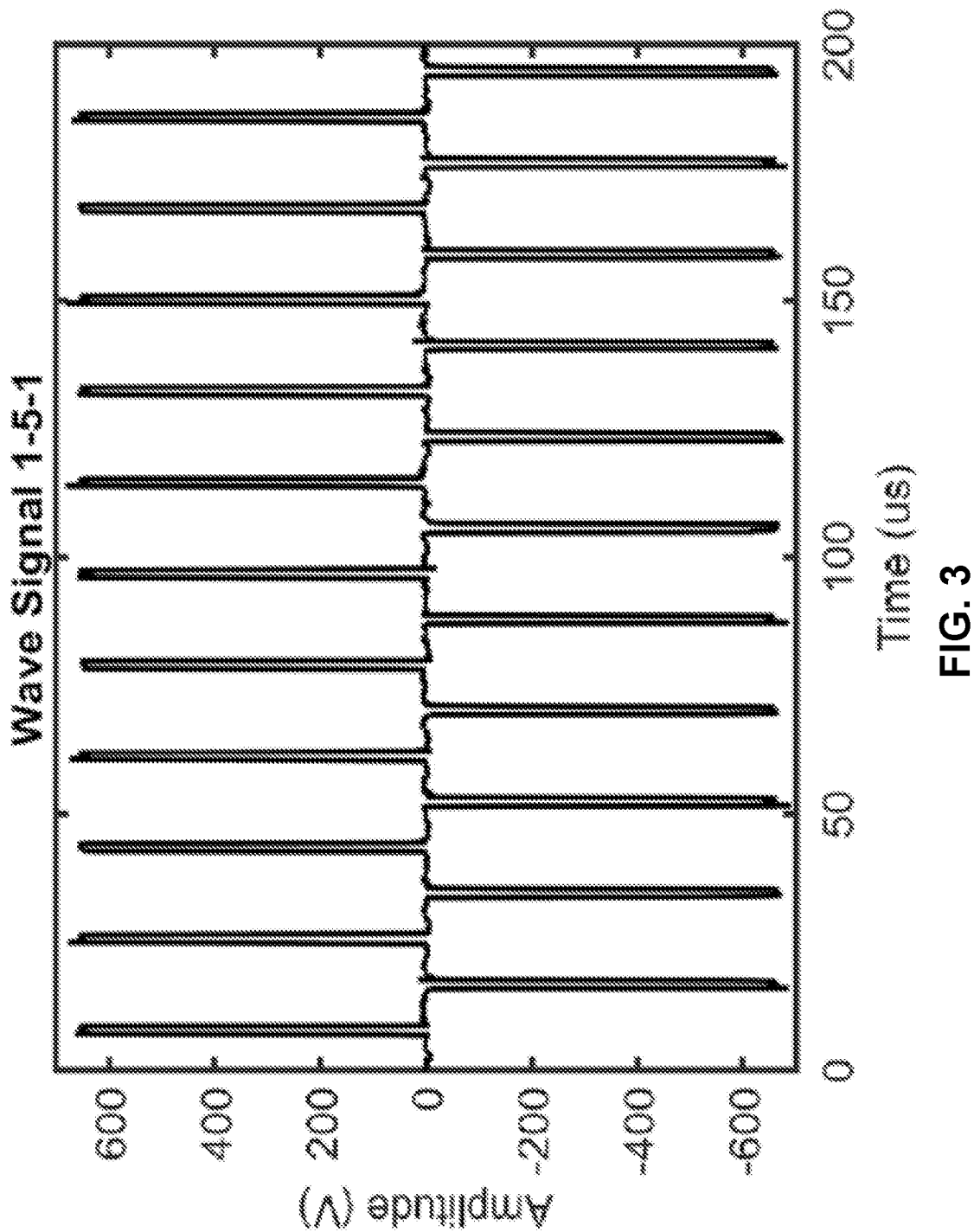
FIG. 3 shows a graph that can demonstrate an example pulse wave form that was applied to hydrogels. A bipolar waveform of 1 µs pulses separated by about a 5 µs delay was used to accomplish electroporation in a hydrogel platform.
Figure 4:
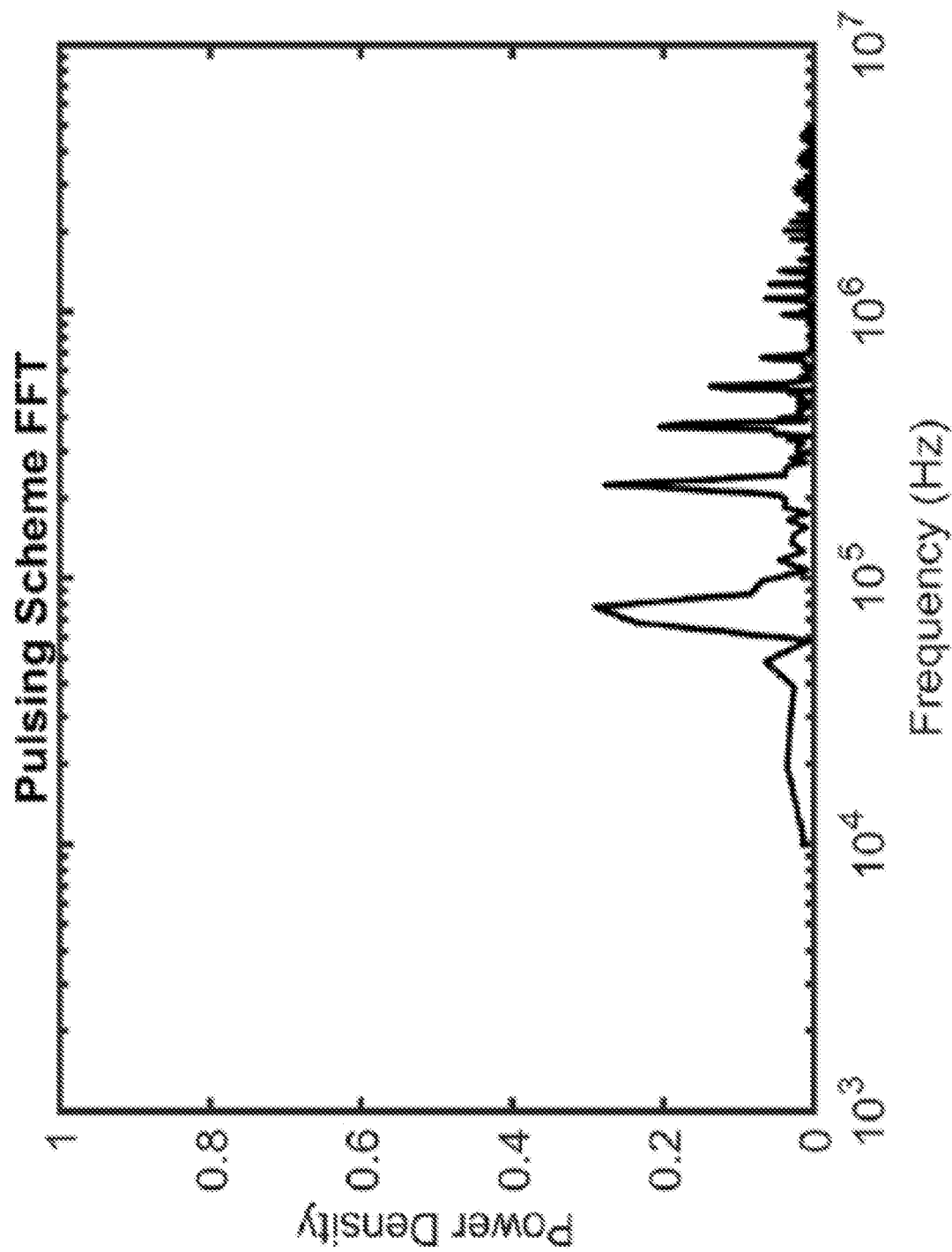
FIG. 4 shows a power-spectrum analysis of the example pulse train of FIG. 3. The amplitude frequency distribution found by fast Fourier transform of experimental pulse trains can demonstrate that the pulse train of 1 µs bipolar pulses separated by about a 5 µs delay can deliver the majority of its power frequencies at about 100 KHz.
Figure 5:
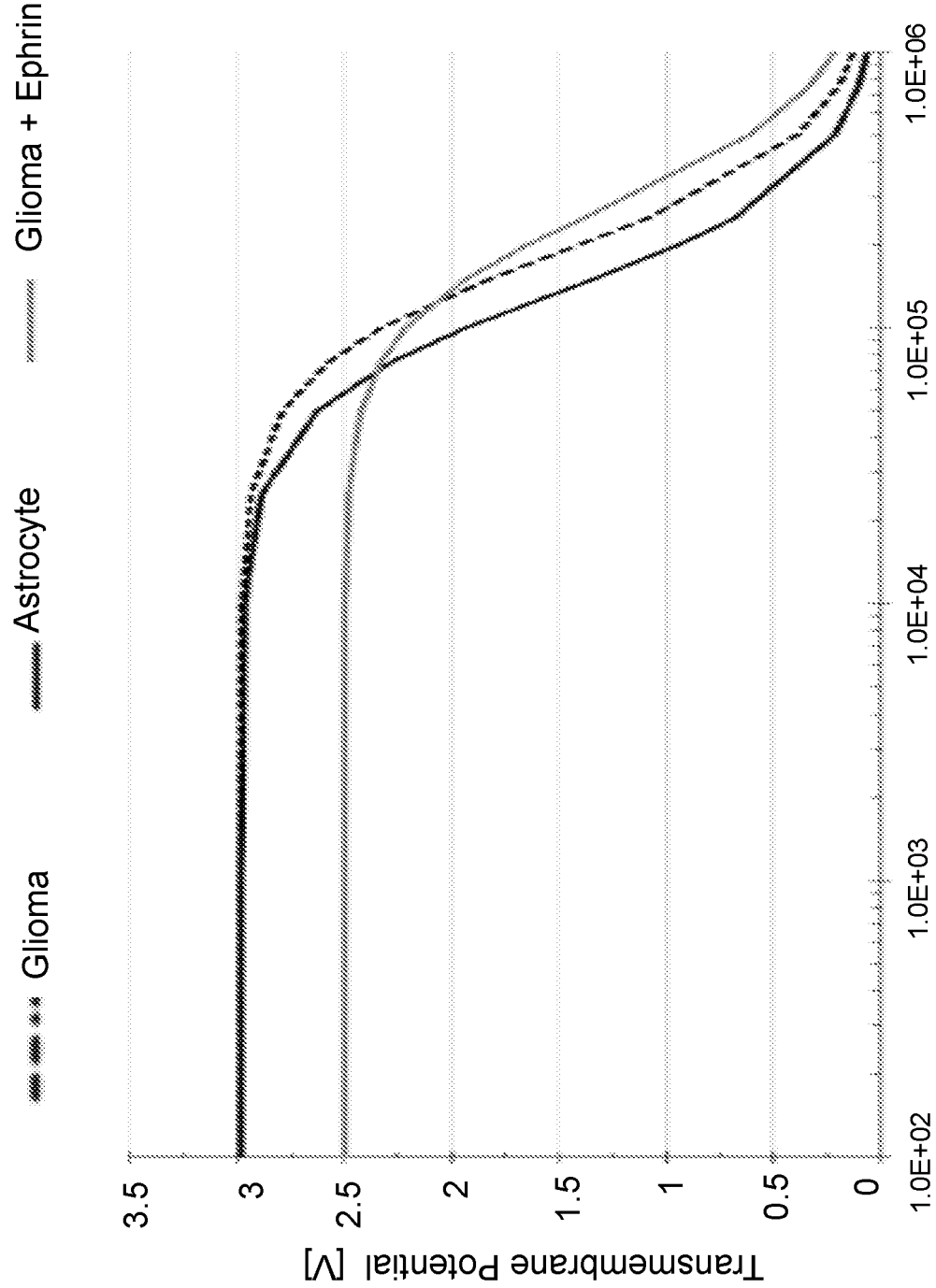
FIG. 5 shows a graph that can demonstrate a single-cell steady-state response to an electric field of about 1000V/cm applied as an alternating-current signal. It was observed that larger cells (U87 and astrocyte) present larger TMPs at lower frequencies. It was observed that cells of larger NCR will have larger TMPs at higher frequencies (>100 kHz).
Figure 6A:
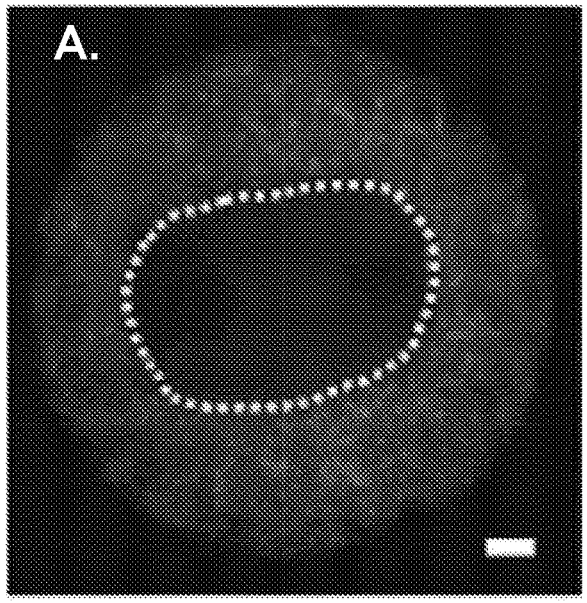
FIGS. 6A-6H show microscopic images that can demonstrate H-FIRE lesion size in malignant glioma cells (U-87, U-251, and DBTRG) and non-malignant (normal) astrocytes (NHAs) after culture of hydrogels in control media (FIGS. 6A-6D) or eA1 supplemented media (FIGS. 6E-6H). It was observed that H-FIRE lesion size for malignant cells was increased relative to the control astrocytes (NHAs). It was also observed that H-FIRE lesions in non-malignant astrocytes (NHAs) remained unchanged with eA1 exposure. Scale bars=1 mm.
Figure 6B:
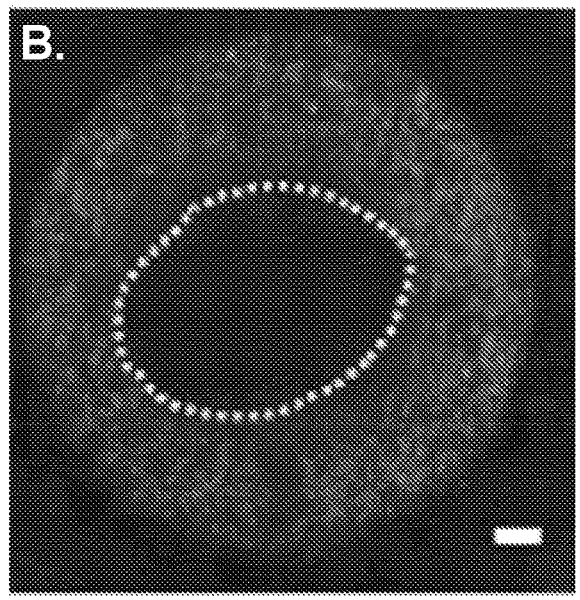
Figure 6C:
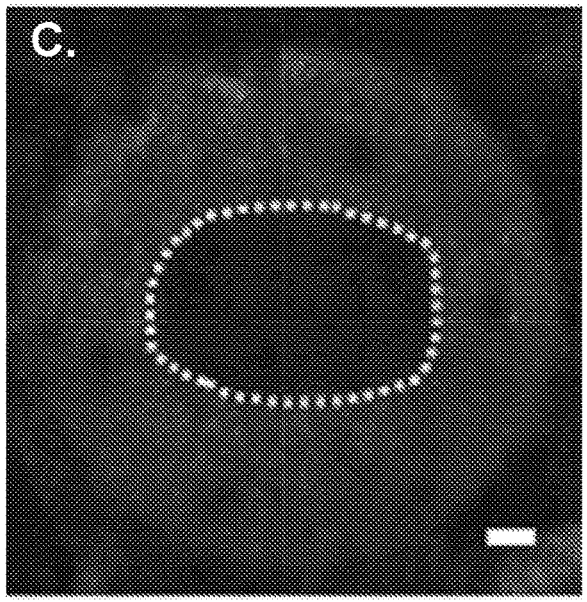
Figure 6D:
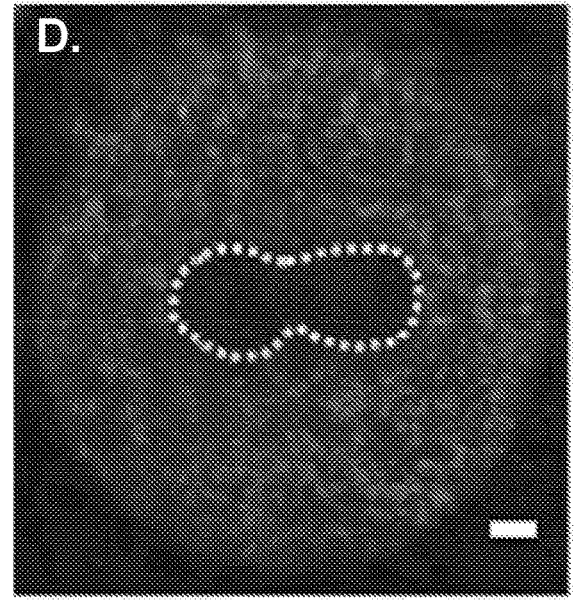
Figure 6E:
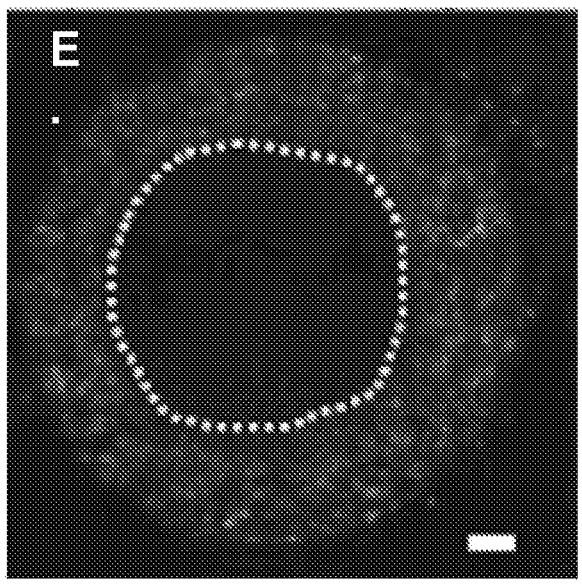
Figure 6F:
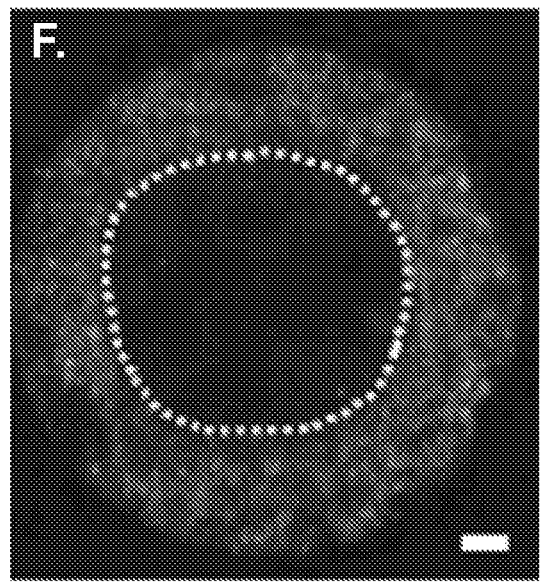
Figure 6G:
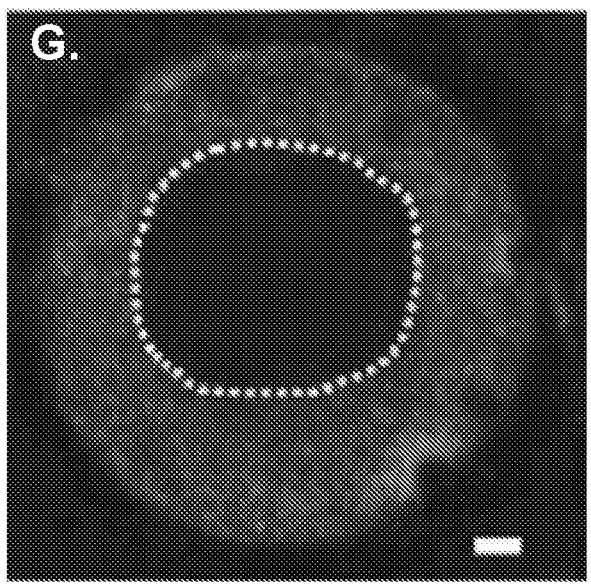
Figure 6H:
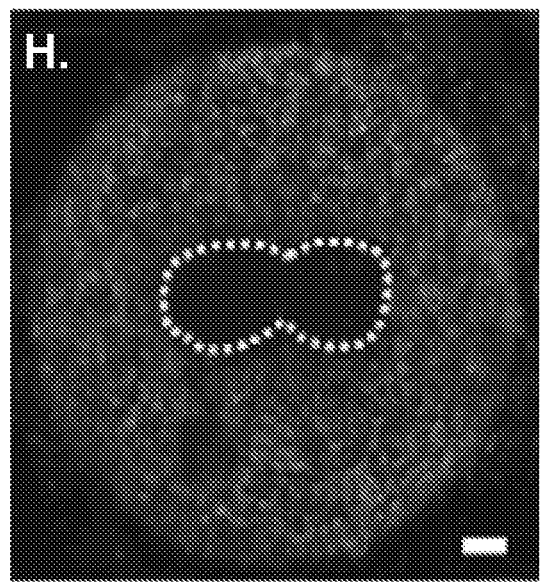

As the duration of the applied pulse is decreased, a greater proportion of the power is concentrated in higher frequency signal content. The experimental pulse train of 1 μs bipolar pulses with a 5 μs delay between pulses (FIG. 3) delivers the majority of its power between 100 kHz and 1000 kHz (FIG. 4). Interestingly, these frequencies correspond to the frequencies predicted to allow for a crossover in TMP for the eA1-induced cell morphologies when exposed to an alternating-current signal (FIG. 5).

Figure 7:
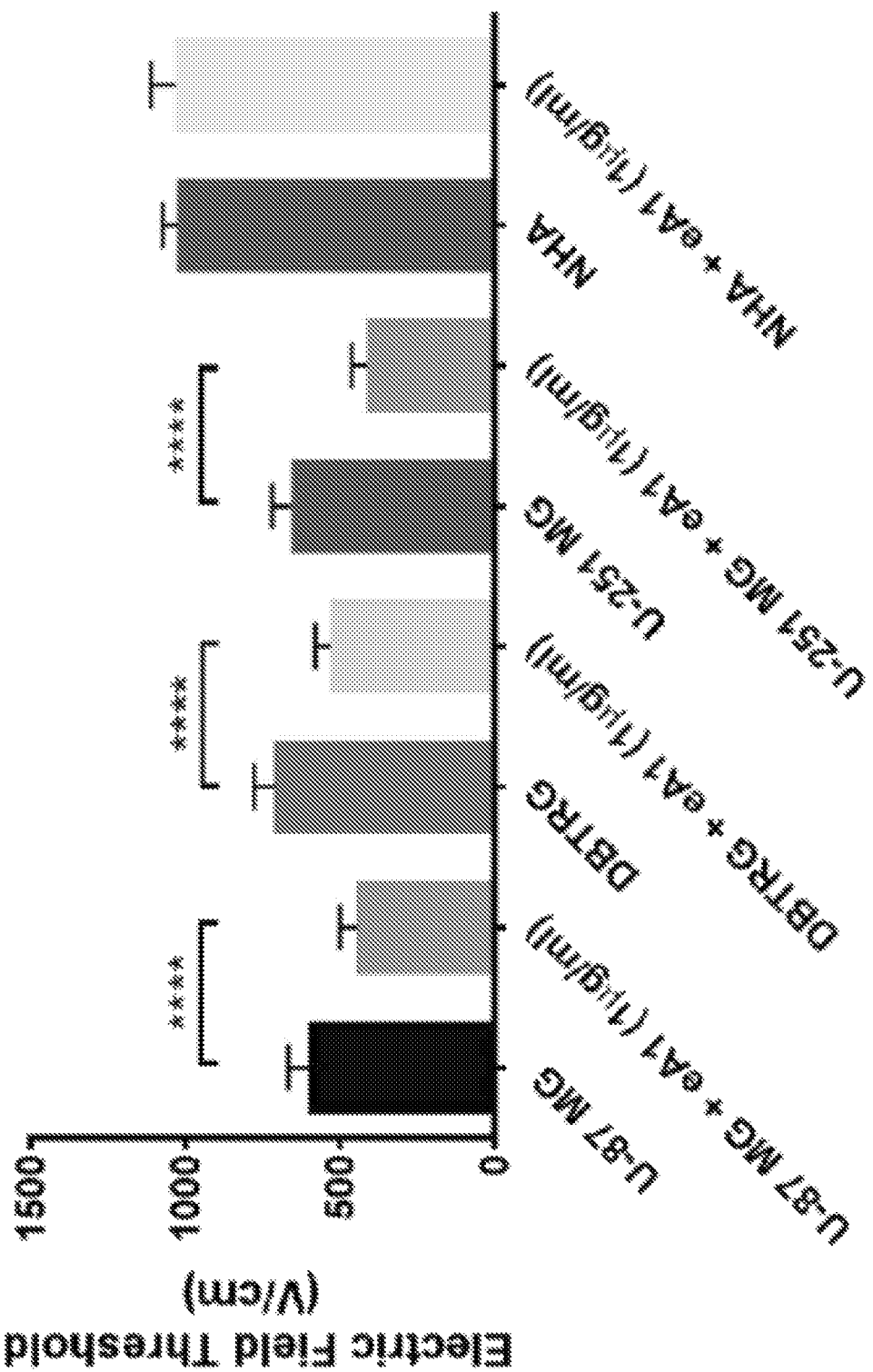
FIG. 7 shows a graph that can demonstrate COMSOL modeling relating lesion size to lethal thresholds. A significant decrease in H-FIRE lethal threshold was observed for malignant cells when treated with eA1 prior to electroporation exposure. No change was observed in H-FIRE lethal threshold for non-malignant cells with eA1 exposure.
Figure 8:
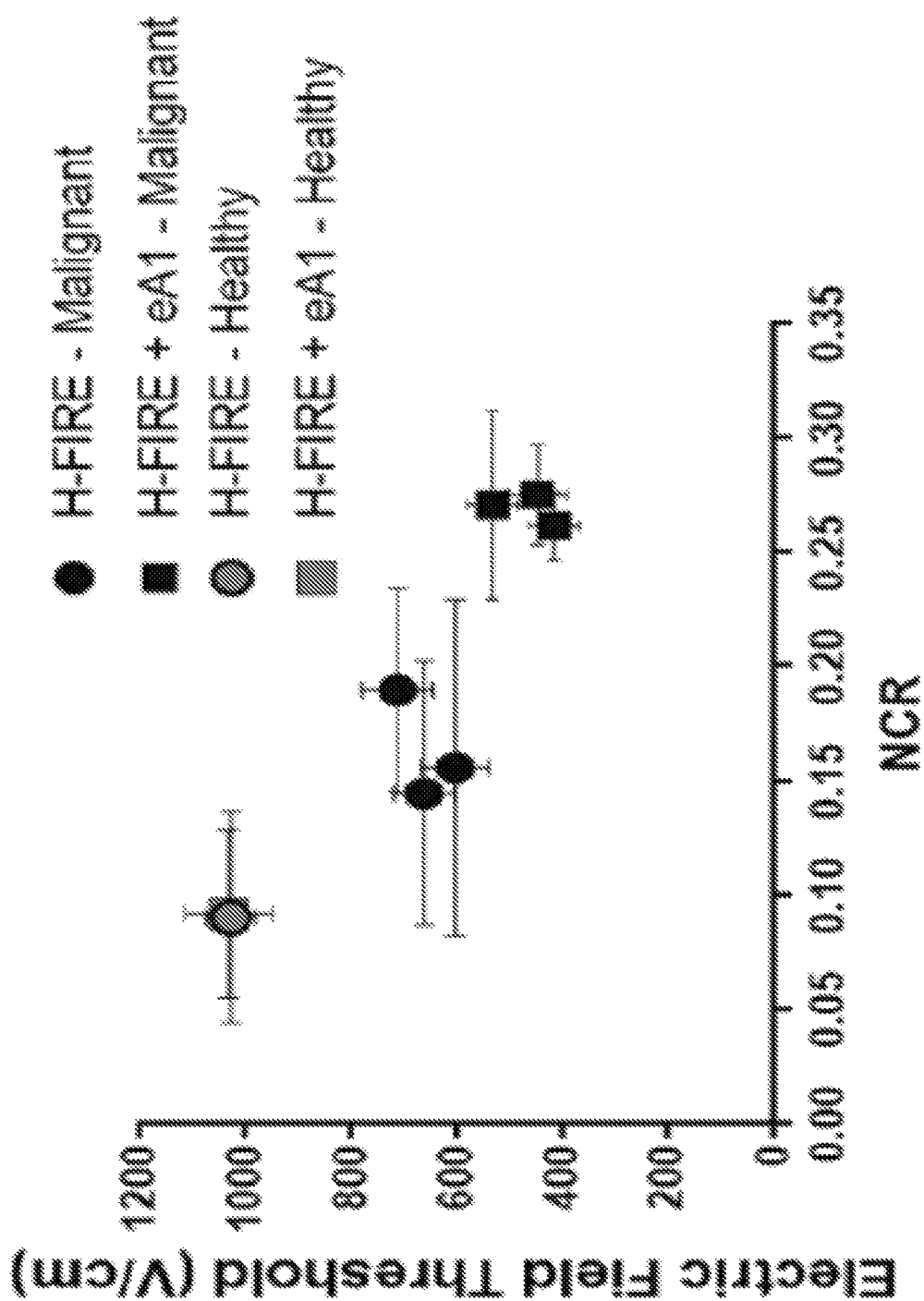
FIG. 8 shows a graph demonstrating a summary of data and can demonstrate a correlation between the average NCR of a given cell type in the hydrogel and the lethal electric-field threshold for that cell type in the hydrogel. Healthy astrocytes (gray markers) were observed to have no change with eA1 treatment. Malignant cells (black markers) were observed to have a decreased lethal electric-field threshold when treated with eA1 to induce an NCR increase. ****p≤ 0.0001.

Morphology change can impact lethal thresholds for electroporation of malignant cells. To determine whether the increase in the NCR in malignant cells led to a change in the H-FIRE threshold as predicted by finite-element modeling, eA1-treated hydrogels were exposed to a regimen of H-FIRE treatment and compared with control hydrogels. Malignant hydrogels treated with eA1 had significantly larger lesions than control hydrogels, whereas non-malignant hydrogels had no significant difference between conditions (FIGS. 6A-6H). The increase in NCR for malignant cells corresponded to a smaller lethal threshold for H-FIRE, whereas the lethal threshold did not change for non-malignant cells (FIG. 7). For U87 cells, under normal conditions, the lethal threshold is 603±65 V/cm (n=8), whereas under treatment with eA1, the lethal threshold is 446±55 V/cm (n=8). For U-251 cells, under normal conditions, the lethal threshold is 662±57 V/cm (n=8), whereas under treatment with eA1, the lethal threshold is 415±48 V/cm (n=8). For DBTRG cells, under normal conditions, the lethal threshold is 712±68 V/cm (n=6), whereas under treatment with eA1, the lethal threshold is 532±48 V/cm (n=6). Lethal thresholds for non-malignant cell types remained unchanged. Control NHA cells are killed at a threshold of 1028±47 V/cm (n=6) and eA1-treated NHA cells have a lethal threshold of 1032±82 V/cm (n=6). For the most responsive cell type, U-251 cells, eA1 treatment resulted in about a 37% decrease in the lethal threshold for H-FIRE therapy.

Figure 9A:
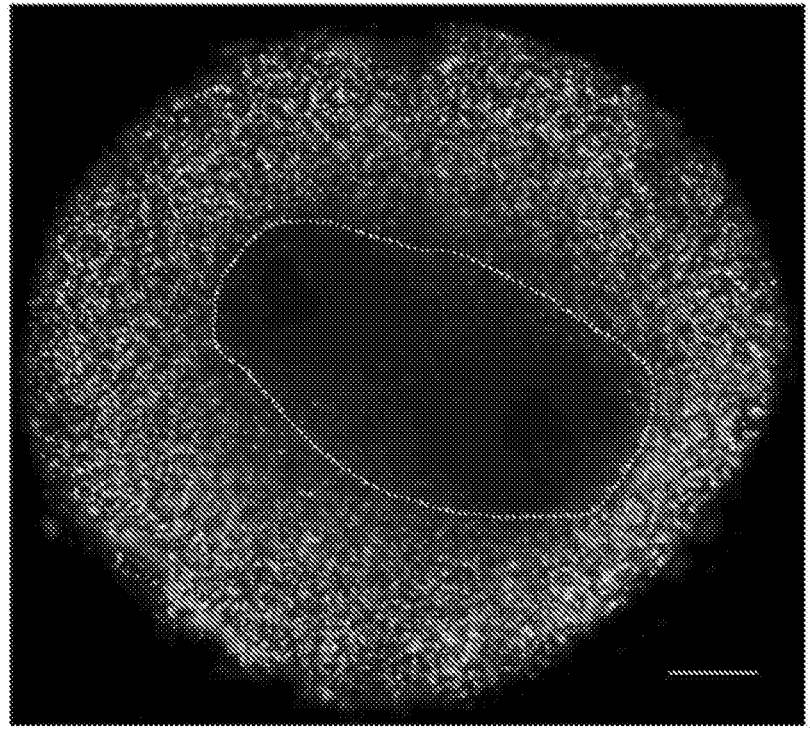
FIGS. 9A-9B show microscopic images of hydrogels seeded with U-251 glioma cells in basal media (FIG. 9A) or U-251 glioma cells cultured in media supplemented with eA1 (FIG. 9B) that can demonstrate IRE lesion size. Scale bars=1 mm. IRE lesion size was observed to be smaller in the U-251 glioma (malignant) cells treated with eA1 compared to control U-251 cells in basal media.
Figure 9B:
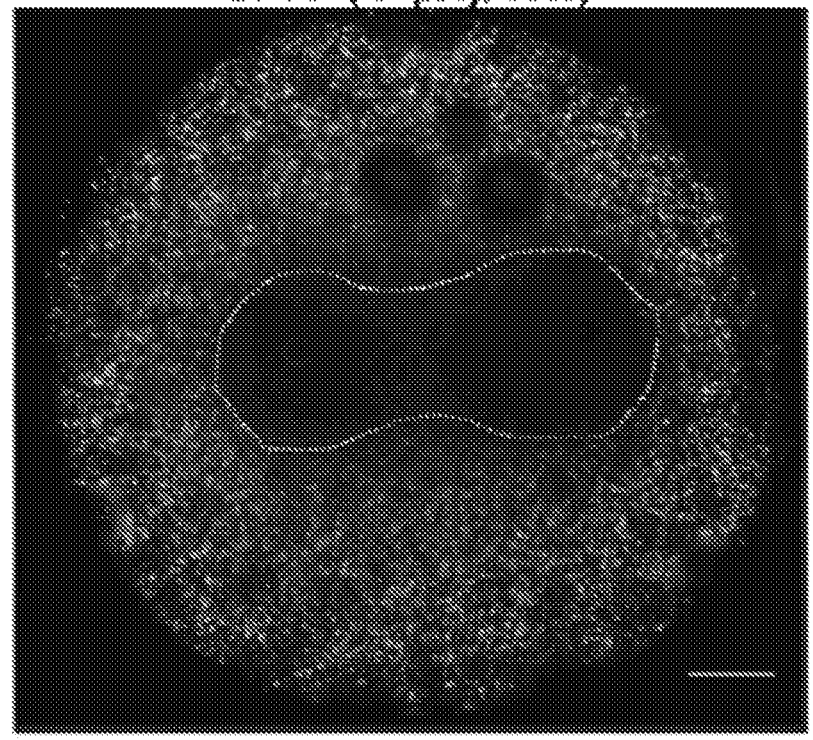
Figure 10:
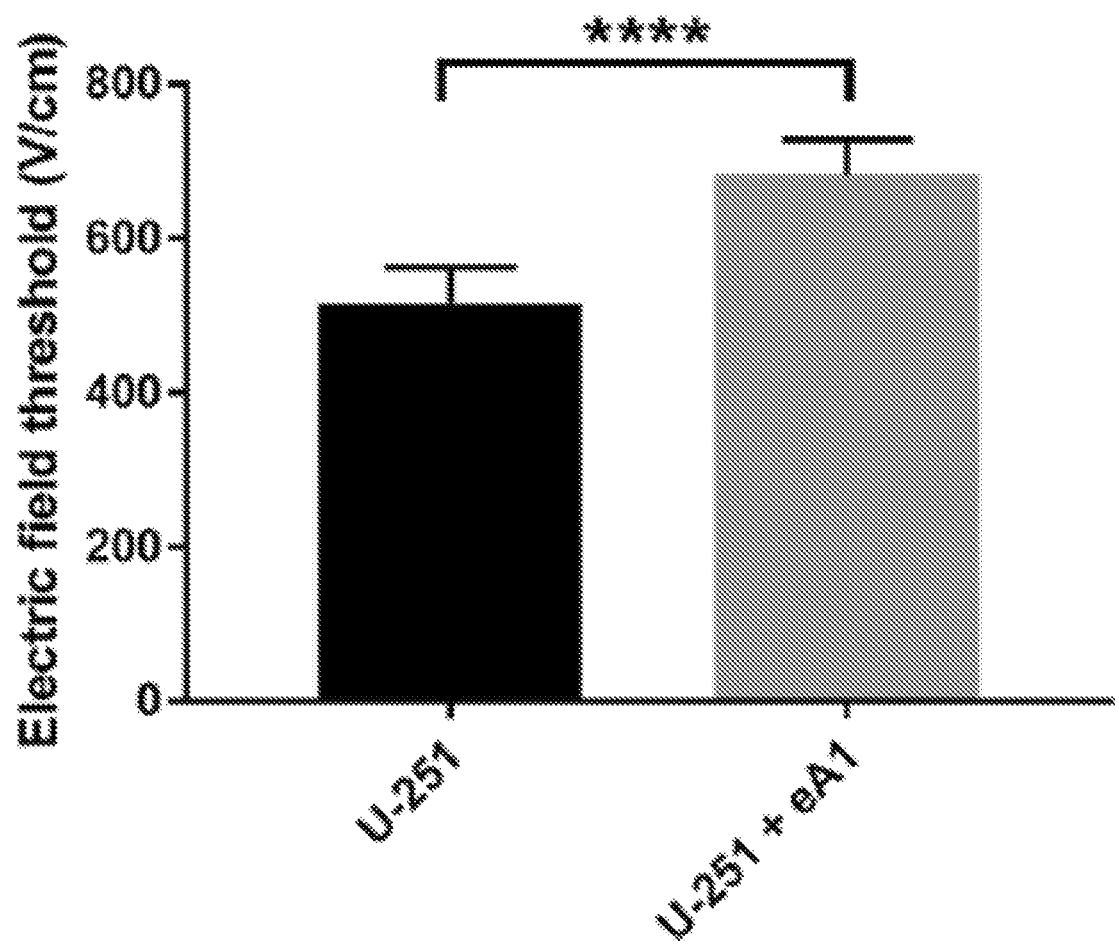
FIG. 10 shows a graph that can demonstrate COMSOL modeling relating lesion size to lethal thresholds. COMSOL modeling demonstrated a significant increase in IRE lethal threshold for U-251 cells when treated with eA1 before electroporation exposure as compared to control cells. n=6; ****p≤ 0.0001.
Figures 11A, 11B, 11C, 11D, 11E, 11F:
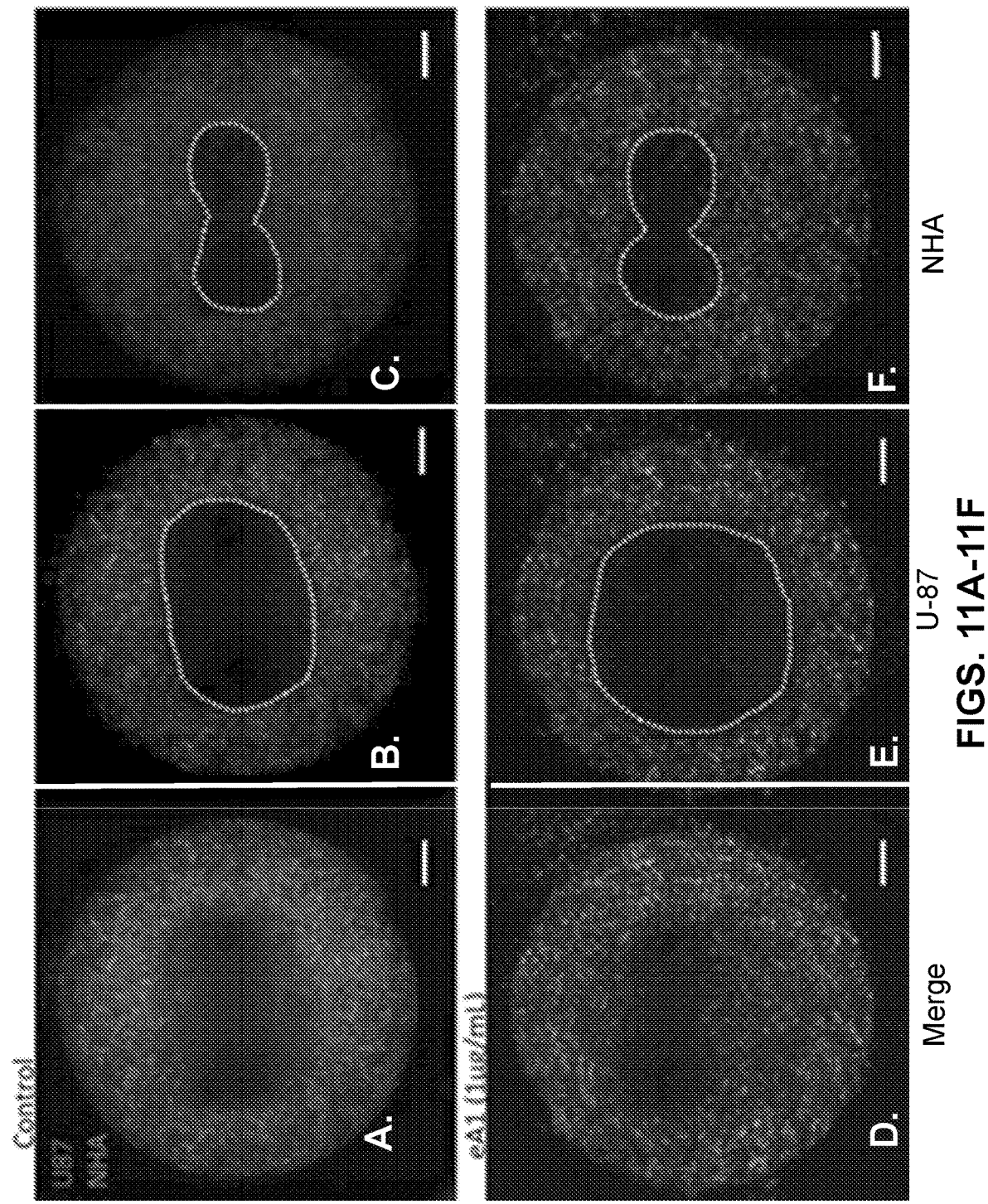
FIGS. 11A-11F show microscopic images that demonstrate lesion sizes in hydrogels co-seeded with malignant cells (U-87) and normal astrocytes (NHAs) and cultured in control (FIGS. 11A-11C) or eA1 supplemented media (FIGS. 11D-11F). It was observed that treatment with eA1 enhanced selectivity of H-FIRE for malignant cells compared to healthy cells in co-culture. The area of ablated malignant cells and live healthy cells (NHAs) was observed to be extended by treating the co-cultured hydrogels with eA1 before H-FIRE exposure.

Similarly, eA1-treated hydrogels were exposed to traditional IRE pulses of 100 ms pulse width to determine whether these lesions would change as a result of the eA1-induced morphology change in treated cells. In contrast to the trend using H-FIRE pulses, IRE lesions of eA1-treated U-251 cells are significantly smaller than control hydrogels of U-251 cells cultured in normal media (FIGS. 9A-9B and 10). U-251 cells cultured in normal media within the hydrogels had an IRE lethal threshold of 517±45 V/cm (n=6). U-251 cells cultured with media containing about 1 mg/mL eA1 within the hydrogels had an IRE lethal threshold of 684±44 V/cm (n=6).

eA1 treatment can enhance malignant cell selectivity of H-FIRE. To demonstrate the enhanced selectivity of malignant cells possible with combination H-FIRE-and-eA1 treatment, co-culture experiments were performed. Hydrogels of NHAs and U-87 GBM cells were cultured in media containing eA1 and then exposed to a regime of H-FIRE pulses. Although selective killing of U87 cells and not NHA cells is achieved in the control condition, the region of U87 killing is significantly enlarged, whereas the NHA lesion remains the same for cells exposed to eA1 (FIGS. 11A-11F).

Discussion

This Example can demonstrate that the cell-size dependence for electroporation-induced cell death can depend on frequency range. Each component of the cell—membrane, cytoplasm, and nuclear membrane—has a characteristic impedance that affects the TMP response to varying degrees depending on the cell morphology. As the capacitance of each part of the cell is dependent on the surface area, the change in morphology induced by eA1 treatment can produce changes in cell capacitance.

It was hypothesized that the effect demonstrated here of high frequency PEFs preferentially ablating cells of smaller volume but higher NCR may be due to changes in impedance of the cytoplasm. If part of the external field is able to bypass the cell membrane and interact with internal components of the cell, the impedances of the cytoplasm and nucleus become important factors. This effect, which can be exploited through treatment with eA1, can be magnified as the volume of the cytoplasm is decreased. Therefore, for high-frequency pulses, the NCR of a cell becomes a significant variable in predicting electroporation response. This finding is significant for the understanding of electroporation theory, because it clearly illustrates that the relationship between cell size and electroporation is closely dependent on waveform frequency, which would impact electroporation protocols both for research and for therapeutic applications.

This Example can demonstrate that molecular targeting with ensuing changes in GBM cell morphology can be used to enhance the selectivity of PEFs to induce tumor cell death. Selectivity, regulated by the NCR, opens up the possibility of enhanced targeted cancer therapy, as malignant cells are known to often have increased NCR compared to normal cells (32, 33). Because the EphA2 receptor is overexpressed specifically on malignant cells in adulthood, the induced morphology change can be exploited in developing combinatorial targeted therapies using H-FIRE. The ability to selectively target cells with increased NCR is significant for the future of GBM treatment, because it may allow for the treatment of diffuse malignant cells that have invaded into normal brain tissue. By lowering the lethal threshold for malignant cells in the outermost regions of the tumor, where selectivity is most important, eA1 treatment may increase the margin of tumor that can safely be ablated with H-FIRE therapy regimes. Though many attempts have been made to use EphA2 as a direct therapeutic target (19, 34), this work is the first that utilizes a resulting morphological change to enhance targeting by combination with a physical therapy in the form of PEFs. It is further noted that short (about 1 μs) pulses in particular are necessary to induce this synergistic tumor cell death response, as we have demonstrated that longer (about 100 μs) IRE pulses of the sort most commonly used for clinical tumor ablation (5,7) become less effective in combination with sub-lethal eA1 treatment in our studies. The results presented here can suggest the ability of such techniques to optimize parameters to further increase the selectivity, with the possibility of efficacy in an in vivo context. The performed power spectral analysis of IRE and H-FIRE pulses indicates that a higher-frequency signal content (>100 kHz) can increase the ability to target cells of a higher NCR.

The EphA2 receptor has been identified as overexpressed in various cancers (35-39) in addition to GBM, suggesting a broader application for the results for treatments in other tumor sites for which more traditional surgical or radiotherapy options may be limited, for example, tumors that surround, for example, sensitive neural or vascular structures. Areas of increased EphA2 expression are important therapy targets, as elevated EphA2 expression has been correlated with higher pathological grade (40) and poor prognosis (41,42). EphA2 is an important target for this synergistic therapy for another important reason, which is that it may allow for the targeting of highly tumorigenic glioma stem cells, which combinatorial treatments may leave behind due to their highly chemoresistant nature (43). EphA2 receptors have been found to be expressed most highly on tumor-initiating cells, with the highest levels of expression in the most aggressive, stem-cell-like mesenchymal subtype (44). Though the EphA2/ephrinA1 interaction has been the subject of our study, multi-ligand cocktails can also be explored to capitalize on other ephrin interactions in cancer.

The findings presented here can highlight the importance of considering the physical phenotypes of cells both for treatment planning and for exploitation to improve treatment efficacy.

REFERENCES FOR EXAMPLE 1

1. Weaver, J. C., and Y. A. Chizmadzhev. 1996. Theory of electroporation: a review. Bioelectrochem. Bioenerg. 41:135-160.
2. Mir, L. M. 2001. Therapeutic perspectives of in vivo cell electropermeabilization. Bioelectrochemistry. 53:1-10.
3. Agerholm-Larsen, B., H. K. Iversen, J. Gehl. 2011. Preclinical validation of electrochemotherapy as an effective treatment for brain tumors. Cancer Res. 71:3753-3762.
4. Davalos, R. V., I. L. Mir, and B. Rubinsky. 2005. Tissue ablation with irreversible electroporation. Ann. Biomed. Eng. 33:223-231.
5. Cannon, R., S. Ellis, R. C. Martin, II. 2013. Safety and early efficacy of irreversible electroporation for hepatic tumors in proximity to vital structures. J. Surg. Oncol. 107:544-549.
6. Onik, G., and B. Rubinsky. 2010. Irreversible electroporation: first patient experience focal therapy of prostate cancer. In Irreversible Electroporation. B. Rubinsky, editor. Springer, pp. 235-247.
7. Martin, R. C., 2nd, D. Kwon, K. Watkins. 2015. Treatment of 200 locally advanced (stage III) pancreatic adenocarcinoma patients with irreversible electroporation: safety and efficacy. Ann. Surg. 262:486-494, discussion 492-494.
8. Neal, R. E., 2nd, J. L. Millar, K. R. Thomson. 2014. In vivo characterization and numerical simulation of prostate properties for nonthermal irreversible electroporation ablation. Prostate. 74:458-468.
9. Lee, E. W., C. Chen, S. T. Kee. 2010. Advanced hepatic ablation technique for creating complete cell death: irreversible electroporation. Radiology. 255:426-433.
10. Guo, Y., Y. Zhang, A. C. Larson. 2010. Irreversible electroporation therapy in the liver: longitudinal efficacy studies in a rat model of hepatocellular carcinoma. Cancer Res. 70:1555-1563.
11. Daniels, C., and B. Rubinsky. 2009. Electrical field and temperature model of nonthermal irreversible electroporation in heterogeneous tissues. J. Biomech. Eng. 131: 071006.
12. Lee, E. W., C. T. Loh, and S. T. Kee. 2007. Imaging guided percutaneous irreversible electroporation: ultrasound and immunohistological correlation. Technol. Cancer Res. Treat. 6:287-294.
13. Bonakdar, M., E. L. Latouche, R. V. Davalos. 2015. The feasibility of a smart surgical probe for verification of ire treatments using electrical impedance spectroscopy. IEEE Trans. Biomed. Eng. 62:2674-2684.
14. Neal, R. E., II, J. H. Rossmeisl, Jr., R. V. Davalos. 2014. In vitro and numerical support for combinatorial irreversible electroporation and electrochemotherapy glioma treatment. Ann. Biomed. Eng. 42: 475-487.
15. Wykosky, J., D. M. Gibo, W. Debinski. 2005. EphA2 as a novel molecular marker and target in glioblastoma multiforme. Mol. Cancer Res. 3:541-551.
16. Hatano, M., J. Eguchi, H. Okada. 2005. EphA2 as a glioma-associated antigen: a novel target for glioma vaccines. Neoplasia. 7:717-722.
17. Liu, D.-P., Y. Wang, D. Xie. 2007. Ephrin-A1 is a negative regulator in glioma through down-regulation of EphA2 and FAK. Int. J. Oncol. 30:865-871.
18. Wykosky, J., E. Palma, W. Debinski. 2008. Soluble monomeric EphrinA1 is released from tumor cells and is a functional ligand for the EphA2 receptor. Oncogene. 27:7260-7273.
19. Wykosky, J., D. M. Gibo, and W. Debinski. 2007. A novel, potent, and specific ephrinA1-based cytotoxin against EphA2 receptor expressing tumor cells. Mol. Cancer Ther. 6:3208-3218.
20. Ferluga, S., R. Hantgan, W. Debinski. 2013. Biological and structural characterization of glycosylation on ephrin-A1, a preferred ligand for EphA2 receptor tyrosine kinase. J. Biol. Chem. 288:18448-18457.
21. Miao, H., E. Burnett, B. Wang. 2000. Activation of EphA2 kinase integrin function and causes focal-adhesion-kinase dephosphorylation. Nat. Cell Biol. 2:62-69.
22. Eppich, H. M., R. Foxall, D. T. Scadden. 2000. Pulsed electric fields for selection of hematopoietic cells and depletion of tumor cell contaminants. Nat. Biotechnol. 18:882-887.
23. Agarwal, A., I. Zudans, S. G. Weber. 2007. Effect of cell size and shape on single-cell electroporation. Anal. Chem. 79:3589-3596.
24. van den Bos, W., D. M. de Bruin, J. J. de la Rosette. 2014. The safety and efficacy of irreversible electroporation for the ablation of prostate cancer: a multicentre prospective human in vivo pilot study protocol. BMJ Open. 4:e006382.
25. Ivey, J. W., E. L. Latouche, S. S. Verbridge. 2015. Targeted cellular ablation based on the morphology of malignant cells. Sci. Rep. 5: 17157.
26. Arena, C. B., M. B. Sano, R. V. Davalos. 2011. High-frequency irreversible electroporation (H-FIRE) for nonthermal ablation without muscle contraction. Biomed. Eng. Online. 10:102.
27. Foster, K. R. 2000. Thermal and nonthermal mechanisms of interaction of radio-frequency energy with biological systems. IEEE Trans. Plasma Sci. 28:15-23.

28. Arena, C. B., M. B. Sano, R. V. Davalos. 2011. Theoretical considerations of tissue electroporation with high-frequency bipolar pulses. Ieee T Bio-Med Eng. 58:1474-1482.
29. Cross, V. L., Y. Zheng, A. D. Stroock. 2010. Dense type I collagen matrices that support cellular remodeling and microfabrication for studies of tumor angiogenesis and vasculogenesis in vitro. Biomaterials. 31:8596-8607.
30. Sano, M. B., C. B. Arena, R. V. Davalos. 2014. In-vitro bipolar nano- and microsecond electro-pulse bursts for irreversible electroporation therapies. Bioelectrochemistry. 100:69-79.
31. Bhonsle, S. P., C. B. Arena, R. V. Davalos. 2015. Mitigation of impedance changes due to electroporation therapy using bursts of high-frequency bipolar pulses. Biomed. Eng. Online. 14 (Suppl 3):S3.
32. White, F. H., and K. Gohari. 1981. Variations in the nuclear-cytoplasmic ration during epithelial differentiation in experimental oralcarcinogenesis. J. Oral Pathol. 10:164-172.
33. Jin, Y., L. J. Yang, and F. H. White. 1995. Preliminary assessment of the epithelial nuclear-cytoplasmic ratio and nuclear volume density in human palatal lesions. J. Oral Pathol. Med. 24:261-265.
34. Boyd, A. W., P. F. Bartlett, and M. Lackmann. 2014. Therapeutic targeting of EPH receptors and their ligands. Nat. Rev. Drug Discov. 13:39-62.
35. Pasquale, E. B. 2010. Eph receptors and ephrins in cancer: bidirectional signalling and beyond. Nat. Rev. Cancer. 10:165-180.
36. Miao, H., and B. Wang. 2012. EphA receptor signaling-complexity and emerging themes. Semin. Cell Dev. Biol. 23:16-25.
37. Zelinski, D. P., N. D. Zantek, M. S. Kinch. 2001. EphA2 overexpression causes tumorigenesis of mammary epithelial cells. Cancer Res. 61:2301-2306.
38. Miyazaki, T., H. Kato, H. Kuwano. 2003. EphA2 overexpression correlates with poor prognosis in esophageal squamous cell carcinoma. Int. J. Cancer. 103:657-663.
39. Thaker, P. H., M. Deavers, A. K. Sood. 2004. EphA2 expression is associated with aggressive features in ovarian carcinoma. Clin. Cancer Res. 10:5145-5150.
40. Li, X., Y. Wang, X. Zhang. 2007. Expression of EphA2 in human astrocytic tumors: correlation with pathologic grade, proliferation and apoptosis. Tumour Biol. 28:165-172.
41. Wang, L.-F., E. Fokas, H.-X. An. 2008. Increased expression of EphA2 correlates with adverse outcome in primary and recurrent glioblastoma multiforme patients. Oncol. Rep. 19:151-156.
42. Liu, F., P. J. Park, M. D. Johnson. 2006. A genome-wide screen reveals functional gene clusters in the cancer genome and identifies EphA2 as a mitogen in glioblastoma. Cancer Res. 66:10815-10823.
43. Liu, G., X. Yuan, J. S. Yu. 2006. Analysis of gene expression and chemoresistance of CD133b cancer stem cells in glioblastoma. Mol. Cancer. 5:67.
44. Binda, E., A. Visioli, A. L. Vescovi. 2012. The EphA2 receptor drives self-renewal and tumorigenicity in stem-like tumor-propagating cells from human glioblastomas. Cancer Cell. 22:765-780.
45. Rubinsky, B. 2007. Irreversible electroporation in medicine. Technology in cancer research & treatment 6:255-259.
46. Asami, K., Y. Takahashi, and S. Takashima. 1989. Dielectric-Properties of Mouse Lymphocytes and Erythrocytes. Biochim Biophys Acta 1010:49-55.
47. Yang, J., Y. Huang, X. J. Wang, X. B. Wang, F. F. Becker, and P. R. C. Gascoyne. 1999. Dielectric properties of human leukocyte subpopulations determined by electrorotation as a cell separation criterion. Biophysical Journal 76:3307-3314.
48. Gascoyne, P. R. C., R. Pethig, J. P. H. Burt, and F. F. Becker. 1993. Membrane-Changes Accompanying the Induced-Differentiation of Friend Murine Erythroleukemia-Cells Studied by Dielectrophoresis. Biochim Biophys Acta 1149:119-126.
49. Sano, M. B., E. A. Henslee, E. M. Schmelz, and R. V. Davalos. 2011. Contactless dielectrophoretic spectroscopy: Examination of the dielectric properties of cells found in blood. Electrophoresis 32:3164-3171.
50. Alberts, B., D. Bray, J. Lewis, M. Raff, K. Roberts, J. D. Watson, and A. Grimstone. 1995. Molecular Biology of the Cell (3rd edn). Trends in Biochemical Sciences 20:210-210.
51. Huang, S.-H., L.-Y. Hung, and G.-B. Lee. 2016. Continuous nucleus extraction by optically-induced cell lysis on a batch-type microfluidic platform. Lab on a Chip 16:1447-1456.

We claim:

1. A method of enhancing electroporation comprising:
   inducing a targeted morphology change in one or more target cells expressing an EphA2 receptor by contacting the one or more target cells with an amount of an EphA2 receptor ligand, wherein the targeted morphology change is a reduction in cytoplasmic size thereby generating an increase in the ratio of nucleus to cytoplasmic size (NCR), and wherein the EphA2 receptor ligand is effective to induce the targeted morphology change; and
   applying, to cells in the plurality of cells expressing the EphA2 receptor ligand and having an increased NCR after contacting the cell, a high-frequency irreversible electroporation (H-FIRE) pulse train.

2. The method of claim 1, wherein the H-FIRE pulse train comprises:
   one or more bursts of bipolar electric pulses, wherein each burst comprises
   two or more electric waveform pulses that alternate polarity with each successive electrical waveform pulse,
   wherein each electric waveform pulse is separated by a delay between each successive electric waveform pulse, and
   wherein each electric waveform pulse comprises a carrier frequency in the range of about 1 kHz to about 1 MHz.

3. The method of claim 2, wherein 1 or 2 bursts are delivered every second.

4. The method of claim 2, wherein each electric waveform pulse is a square wave.

5. The method of claim 2, wherein the delay between each successive electric waveform pulse ranges from about 0.5 µs to about 10 µs.

6. The method of claim 2, wherein the delay between each successive electric waveform pulse is about 5 µs.

7. The method of claim 2, wherein each electric waveform pulse is applied for about 250 ns to about 2 µs.

8. The method of claim 2, wherein each electric waveform pulse is applied for about 1 µs.

9. The method of claim 2, wherein in the carrier frequency is about 200 kHz.

10. The method of claim 2, wherein an output voltage of the H-FIRE pulse train ranges from about 500 V to about 5000 V.

11. The method of claim 2, wherein an output voltage of the H-FIRE pulse train results in a voltage-to-distance ratio of about 2000 V/cm.

12. The method of claim 1, wherein the one or more target cells over express a EphA2 receptor as compared to a normal cell.

13. The method of claim 1, wherein the one or more target cells are one or more cancer cells.

14. The method of claim 1, wherein the one or more target cells are one or more malignant cancer cells.

15. The method of claim 1, wherein the one or more target cells are one or more breast cancer cells, one or more melanoma cells, one or more ovarian cancer cells, one or more lung cancer cells, one or more glioma cells, one or more bladder cancer cells, one or more prostate cancer cells, one or more esophageal cancer cells, one or more renal cancer cells, one or more colon cancer cells, one or more pancreatic cancer cells, or one or more vulvar cancer cells.

16. The method of claim 1, wherein the EphA2 receptor ligand is an ephrin.

17. The method of claim 1, wherein the EphA2 receptor ligand is ephrin A1.

18. The method of claim 1, wherein the one or more target cells are in a subject.

19. A method of selectively ablating one or more target cells responsive to an EphA2 receptor ligand in a subject in need thereof, the method comprising:

administering to the subject an amount of an EphA2 receptor ligand thereby inducing a targeted morphology change in one or more target cells expressing an EphA2 receptor, wherein the targeted morphology change is a reduction in cytoplasmic size thereby generating an increase in the ratio of nucleus to cytoplasmic size (NCR), and wherein the EphA2 receptor ligand is effective to induce the targeted morphology change; and applying a high-frequency irreversible electroporation (H-FIRE) pulse train to a location on or within the subject after administering the amount of the EphA1 receptor ligand.

* * * * *